US008718945B2

(12) United States Patent
Berg

(10) Patent No.: US 8,718,945 B2
(45) Date of Patent: May 6, 2014

(54) METHODS FOR CLASSIFICATION OF TOXIC AGENTS AND COUNTERAGENTS

(75) Inventor: Ellen L. Berg, Palo Alto, CA (US)

(73) Assignee: DiscoveRx Corporation, Fremont, CA (US)

( * ) Notice: Subject to any disclaimer, the term of this patent is extended or adjusted under 35 U.S.C. 154(b) by 612 days.

(21) Appl. No.: 12/594,192

(22) PCT Filed: Mar. 28, 2008

(86) PCT No.: PCT/US2008/058784
§ 371 (c)(1),
(2), (4) Date: May 3, 2010

(87) PCT Pub. No.: WO2008/121896
PCT Pub. Date: Oct. 9, 2008

(65) Prior Publication Data
US 2010/0235104 A1 Sep. 16, 2010

Related U.S. Application Data

(60) Provisional application No. 60/920,985, filed on Mar. 30, 2007.

(51) Int. Cl.
*G06F 19/00* (2011.01)
*G06F 19/12* (2011.01)

(52) U.S. Cl.
CPC ...................................... *G06F 19/12* (2013.01)
USPC ................... 702/19; 702/20; 703/11; 703/12; 707/700

(58) Field of Classification Search
CPC .................. G01N 33/5038; G01N 2015/1006; G01N 33/5005; G01N 33/5023; G01N 33/5041; G01N 2500/10; G01N 2800/00; G01N 2800/60; G01N 33/6893; G01N 15/1475; G01N 17/008; G01N 17/043; G01N 2015/1472
See application file for complete search history.

(56) References Cited

U.S. PATENT DOCUMENTS

| | | | |
|---|---|---|---|
| 6,656,695 B2 | 12/2003 | Berg et al. | |
| 6,763,307 B2 | 7/2004 | Berg et al. | |
| 7,266,458 B2 | 9/2007 | Plavec et al. | |
| 2004/0063088 A1 | 4/2004 | Berg et al. | |
| 2004/0067507 A1 | 4/2004 | Nolan et al. | |
| 2004/0157269 A1 | 8/2004 | Berg et al. | |
| 2007/0072246 A1 | 3/2007 | Berg et al. | |
| 2007/0087344 A1 | 4/2007 | Plavec et al. | |
| 2007/0135997 A1 | 6/2007 | Hytopoulos | |
| 2008/0020417 A1 | 1/2008 | Rosler et al. | |
| 2008/0064041 A1 | 3/2008 | Plavec et al. | |
| 2009/0118133 A1 | 5/2009 | Melrose et al. | |
| 2009/0304769 A1 | 12/2009 | Kunkel et al. | |
| 2010/0093613 A1 | 4/2010 | Kunkel et al. | |

FOREIGN PATENT DOCUMENTS

WO 2004/094992 11/2004

OTHER PUBLICATIONS

Berg; et al., "Biological complexity and drug discovery: a practical systems biology approach", Selected System Biology papers from the International Conference on Foundations of Systems Biology in Engineering (FOSBE 2005), 152(4):201-206.

*Primary Examiner* — Mary Zeman
(74) *Attorney, Agent, or Firm* — David J. Aston; Peters Verny, LLP

(57) ABSTRACT

Methods and systems for evaluating biological dataset profiles relating to toxic agents including candidate pharmaceuticals, environmental agents, biowarfare and chemical warfare agents are provided, where datasets comprising information for multiple cellular parameters are compared and identified, and used in the evaluation of candidate agents.

8 Claims, 9 Drawing Sheets

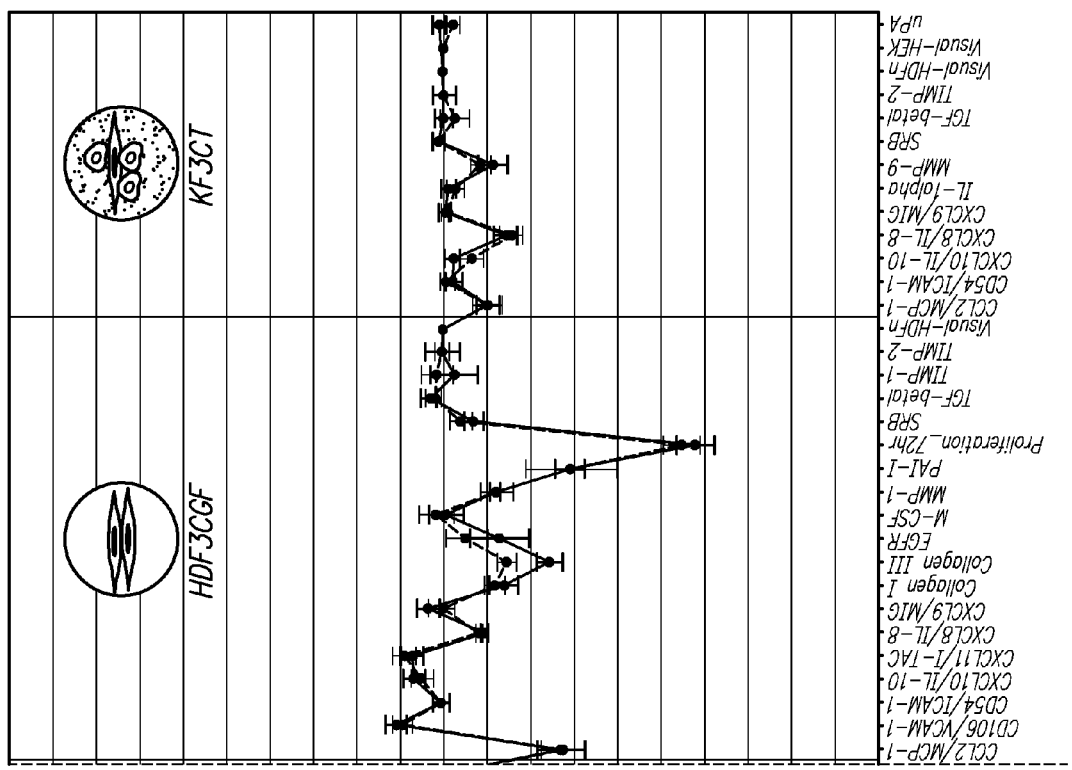

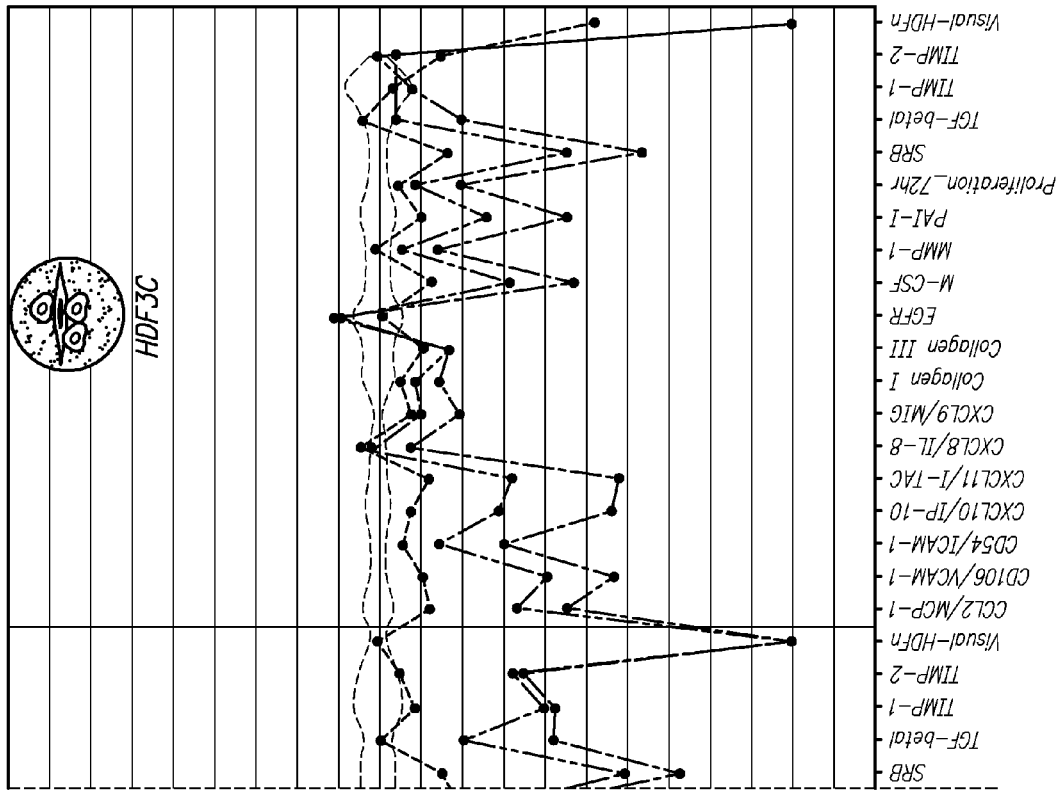

METHODS FOR CLASSIFICATION OF TOXIC AGENTS AND COUNTERAGENTS

FIELD OF THE INVENTION

The present invention provides methods for classification of toxic or potentially toxic agents, such as natural or synthetic organic or bioactive molecules used in pharmaceutical drug discovery, environmental chemicals, and other bioactive materials, as well as biowarfare and chemical warfare agents, according to their mechanism of action, and identification of countermeasure agents. The present invention also provides methods for selection among a group of agents for those with reduced toxicity.

BACKGROUND OF THE INVENTION

Drug toxicity in humans has been difficult to predict and thus has elicited an expensive toll on pharmaceutical research productivity. Unexpected toxicities account for 30% of drug failures in clinical studies and most post marketing drug withdrawals (Kola and Landis (2004) Nat Rev Drug Discov. 3:711-5). Predicting drug side effects has been complicated by the fact that drugs have the potential to subvert normal cellular and physiological processes by a variety of mechanisms.

Toxic agents, including chemical warfare (CW) threat agents, biowarfare agents, as well as pharmaceutical substances can subvert normal cellular processes by a variety of mechanisms. However, despite the diversity of molecular mechanisms and the potential for development of new threat agents with novel mechanisms, common signaling pathways and regulatory processes can be identified. Toxicities can result from specific on- or off-target activities that result in cell death or apoptosis (e.g. inhibition of the anti-apoptotic molecule XIAP); mitochondrial dysfunction (e.g. blocking mitochondrial electron transport); endoplasmic reticulum stress (e.g. proteasome inhibition), or other cell damage; or by interfering with physiologically important feedback mechanisms (e.g. hERG channel). While assessment of some of these activities is standard practice in preclinical development, the assays and cell types employed for many of these are not relevant to the human disease setting and do not predict outcomes in man.

Drugs can also induce toxicity as a consequence of metabolic activation, and transformation into reactive electrophiles that can covalently bind with proteins or DNA, or deplete glutathione (Liebler and Guengerich (2005) Nat. Rev. Drug Discov. 4:410-420). Depending on the targets of these reactions and exposure variables, toxic drug effects can include tissue damage (e.g. liver or heart), allergic and immune reactions, as well as neoplasia. Unfortunately, due to the large number and complex regulation of drug metabolizing enzymes, the ability to predict metabolites and their associated toxicological risks has been limited (Stevens, (2006) Chem. Res. Toxicol. 19:1393-1401; Baillie, Chem. Res. Toxicol (2008) 21:129-137). Cell systems that provide an enhanced sampling of drug metabolizing enzymes may assist in the discovery of toxic metabolites.

Toxic agents, including cellular or metabolic poisons, as well as vesicants, may trigger apoptosis and necrosis pathways directly in exposed tissues (see Li et al. (2005) Toxicol Sci. 86:116-24; Rosenthal et al. (2001) J Invest Dermatol. 117:1566-73). Secondary effects on other cells and tissues also contribute to mortality and morbidity. These can involve inflammatory pathways that are triggered by the initial tissue damage, for example, from exposure to sulfur mustard. Inflammatory pathways can alter cell responses to stress and toxic stimuli, and can themselves be modulated by cell stress and metabolic pathways. (See Wellen et al. (2005) J Clin Invest. 115:1111-9; Cowan et al. (2003) J Appl Toxicol. 23:177-86). Inflammatory and proteolysis pathways have been implicated in the toxicity of both nerve and blister agents.

An understanding of the interaction of inflammatory and cell death pathways is of high interest for the development of effective countermeasures, particularly with respect to chemical and biowarfare agents. Desirable countermeasures include those that are applicable to multiple agents within a class. Potential countermeasures include anti-inflammatory drugs, protease inhibitors, and inhibitors of poly ADP ribose polymerase-1 (PARP-1). Bifunctional compounds containing anti-cholinesterase functional groups coupled to non-steroidal anti-inflammatory drugs have been recently described as potential therapeutic agents for nerve and blister agents. Serine protease inhibitors have shown efficacy in prolonging survival in animals exposed to soman, an organophosphate nerve agent, and may have activity against sulfur mustard. Inhibitors of PARP-1, a DNA repair enzyme that has also been shown to regulate cell death in addition to catalyzing the synthesis of ADP-ribose polymers, may have utility in nerve-agent induced neuronal degeneration as well as sulfur mustard skin damage. A better understanding of the pathologic mechanisms of action of chemical threat agents will help identify additional therapeutic candidates, as well as new therapies with potential utility against novel threat agents.

The development of effective countermeasures against toxic agents is of great military and public interest. Preferably, countermeasures will include approaches that protect the targeted cellular pathways and are applicable to multiple agents. The development of countermeasures may require characterization of intra and inter cellular responses to diverse toxic agents, methods for characterizing the mechanism of action of diverse toxic agents, and a method for rapidly identifying appropriate countermeasures. The present invention addresses these issues.

In the case of pharmaceutical agents, the identification of compounds that are least likely to induce toxicity in patients is of great importance. The present invention, through its ability to identify compounds with secondary or untoward activities, provides a method for selecting agents with reduced toxicity potential.

SUMMARY OF THE INVENTION

The present invention provides methods and systems for evaluating biological dataset profiles relating to the toxicity of biologically active agents, where datasets comprising information for multiple cellular parameters are compared and identified. Classification of toxicity is based on the statistical analysis of protein datasets generated from a panel of complex primary human cell-based assays. This technology detects and distinguishes a broad range of cellular signaling pathway and toxicity mechanisms and is suitable for determining, for example, mechanism of toxicity in an agent, and/or mechanisms of action. The methods of the invention also find use in the evaluation of candidate agents for their suitability as countermeasures against toxic agents.

The methods of the invention provide high-content screening approaches to measure potential toxic events in cell-based assays, in particular those using primary human cells, or cell lines well-suited to toxicity models, in particular using panels of primary human cell types (vascular, epithelial, mesenchymal, blood cell types, etc.) in complex co-culture and activation formats to model human tissue states. Assays of the invention provide a functional signature of the response of diverse human primary cell types in physiologically relevant environments to the tested compounds, and thus represent a reflection or mimic of human tissue responses. These functional profiles are highly reproducible and diagnostic of compound mechanisms, and are ideally suited for chemical comparison and prioritization. Readout parameters such as cell surface or secreted proteins, lipid mediators, total cellular protein, etc., provide toxicological markers such as cell viability, mitochondrial function, nuclear morphology, oxidative stress, apoptosis, membrane permeability as well as important signaling pathways such as DNA damage and repair, cell proliferation, MAPK, SAPK, or inflammation. Together these assays provide a broad coverage of human tissue biology, reducing the chance of missing toxicity mechanisms (false negatives), such as cell type-selective mechanisms. The design of these assays to more closely reflect human in vivo cellular physiology provides enhanced relevance to human exposure, as compared to transformed cell lines or animal models.

A typical dataset of the invention comprises readouts from multiple cellular parameters resulting from exposure of cells, e.g. primary cells, particularly primary human cells, to a toxic agent. The cells are optionally stimulated in one or more, two or more, or three or more different cellular signaling pathways, where such stimulation is effected by culturing the cells in the presence of biologically active factors. Pathways of interest include, without limitation, those involved in cellular models of vascular inflammation, monocyte/macrophage responses, T cell effector responses, fibrosis and skin biology, including novel systems modeling responses at epithelial surfaces. Cellular parameters may also be determined by contacting the cells with candidate toxic agent countermeasures.

Datasets may include control datasets, and/or profile datasets that reflect the parameter changes in a cell culture following exposure to known agents. Known agents may include those having acceptable therapeutic activities against toxic agents as well as those exemplifying undesirable side effects. For analysis of multiple context-defined systems, the output data from multiple systems may be concatenated. Profiles of selected toxic agents and other representative agents may be used to populate a database of induced BioMAP® responses. Such databases allow the development of standardized, automated informatics approaches for classifying chemical threat agents and identifying induced human cellular responses and processes based on BioMAP® toxic responses, database query, and profile analyses. In such classification methods, computational methods are used for classification of toxic agents (e.g. mechanistic identification) by statistical analysis of induced profiles.

BRIEF DESCRIPTION OF THE DRAWING

FIG. 3. Cluster analysis of BioMAP® profiles of 40 toxic agents with diverse mechanisms. Pairwise correlation (Pearson's metric) of 40 compounds of diverse MoA (Table 4) according to BioMAP® profiles in 4 BioMAP® systems was performed, then a.

Function Similarity Map was generated by subjecting the correlation data to multidimensional scaling. Compound relationships that are significantly similar are indicated by the lines drawn between compound profiles.

Figure 4A:
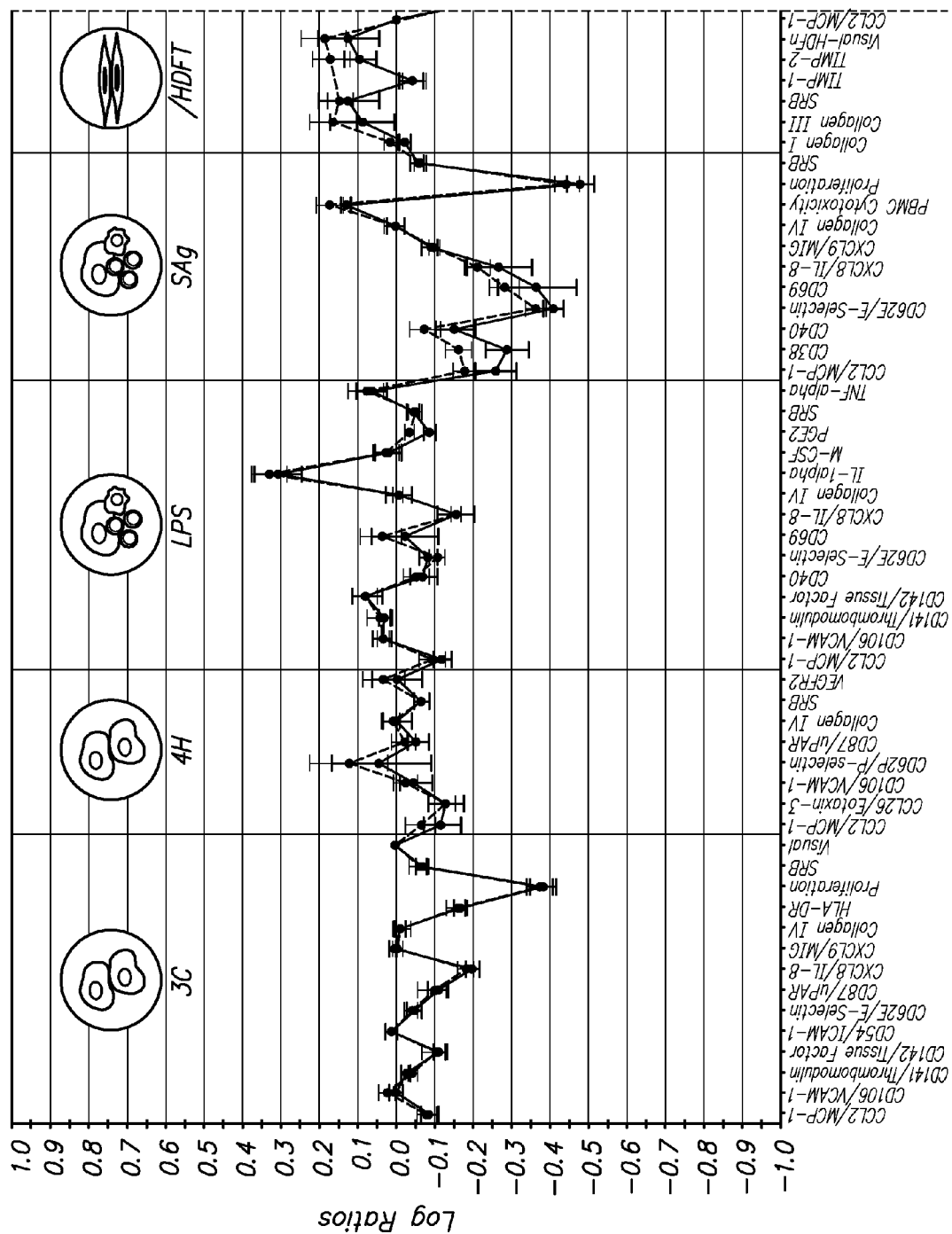

FIG. 4. BioMAP® of mitochondrial complex III inhibitor, myxothiazol. Myxothiazol is an methoxyacrylate-containing inhibitor of the Qo site of the cytochrome bc1 complex in the mitochondrial electron transport chain. Key features of the myxathiazol profile include inhibition of MCP1 in several systems, inhibition of proliferation, T cell activation, and upregulation of IL1 and VCAM (HDF cells).

Figure 5A:
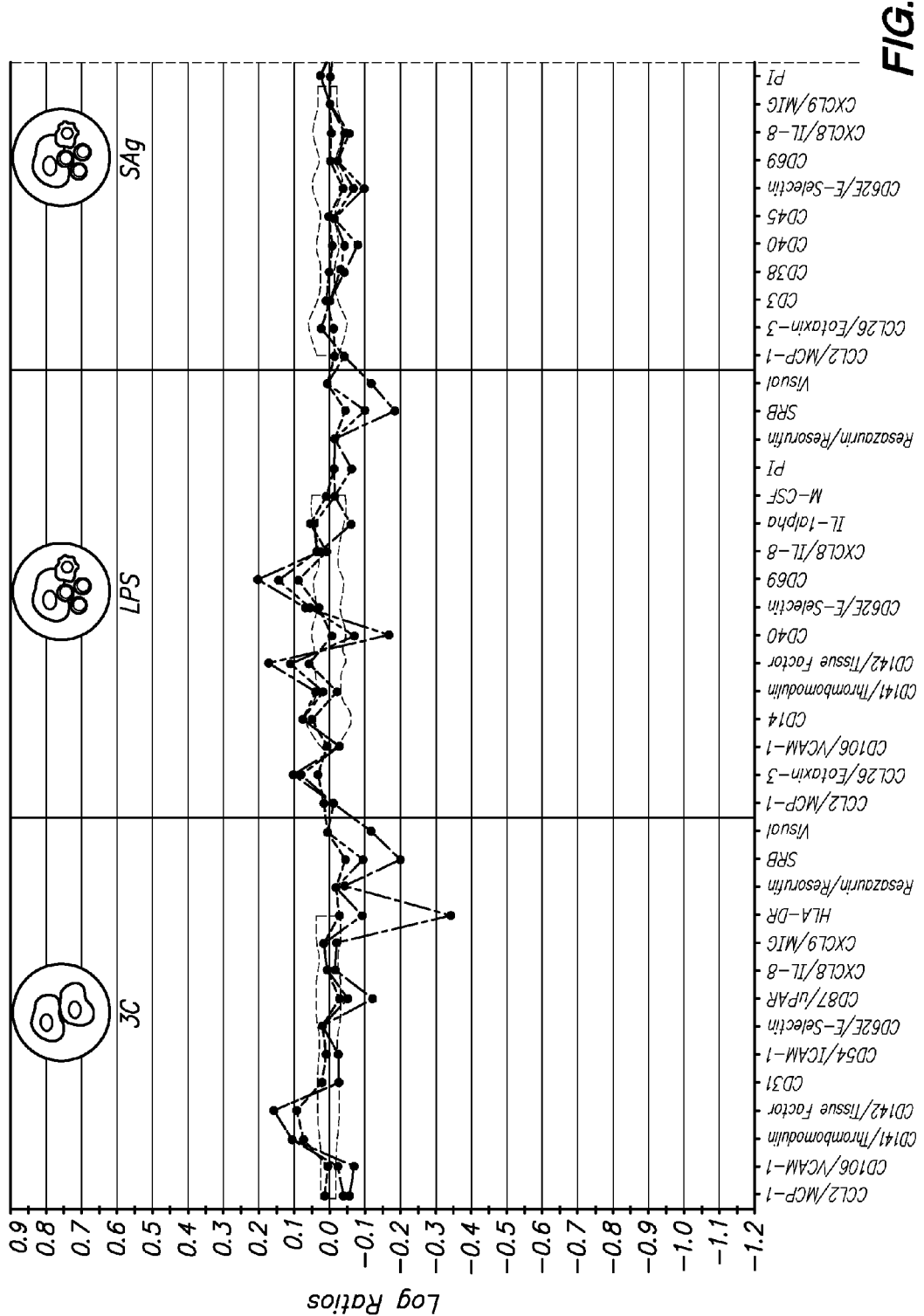
Figure 5B:
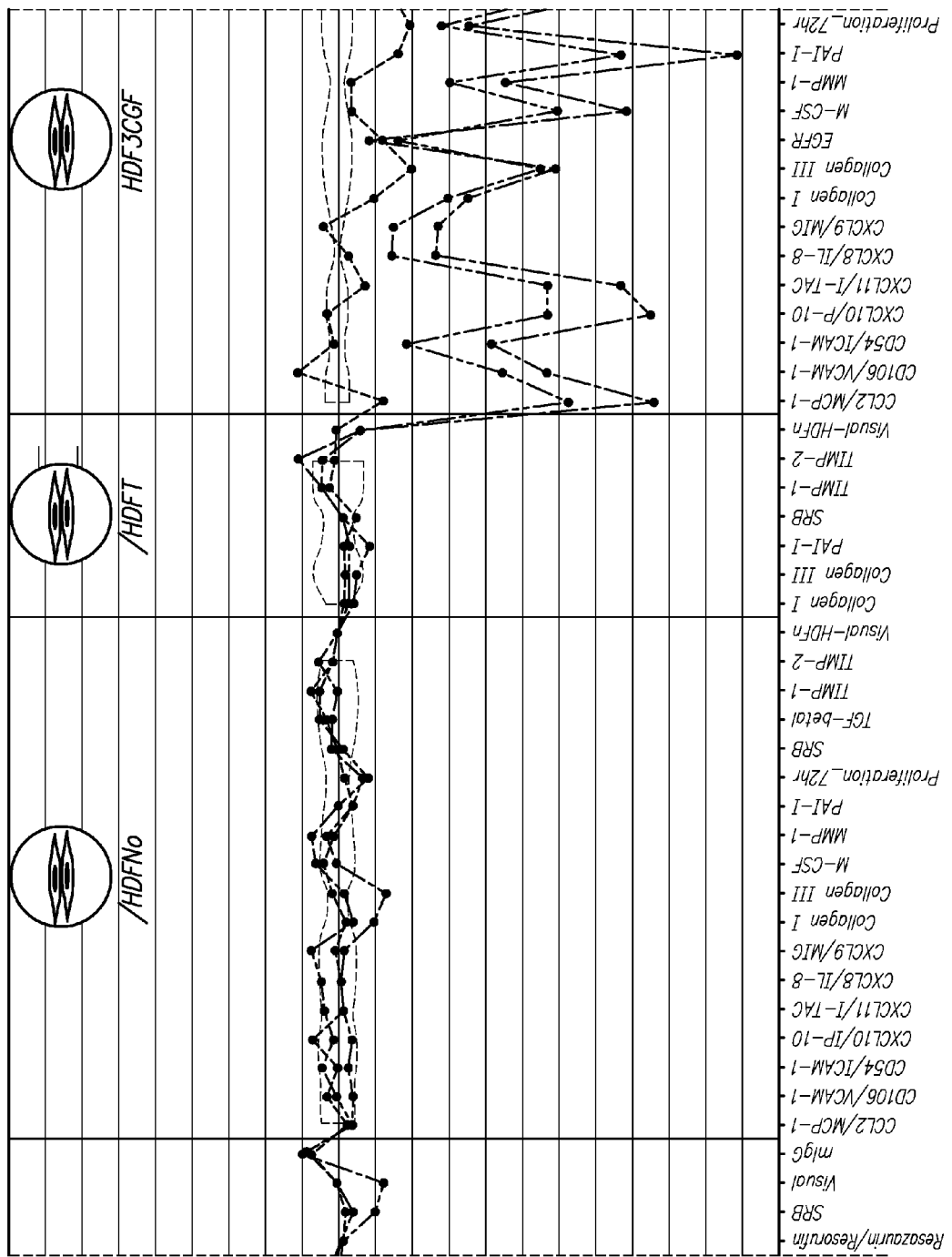

FIG. 5. BioMAP® of PI-3 kinase inhibitor, wortmannin. Wortmannin is a fungal metabolite that inhibits PI-3 kinase. Wortmannin is selectively toxic to fibroblasts in inflammatory BioMAP® systems (HDF3CGF and HDF3C).

Figure 6:
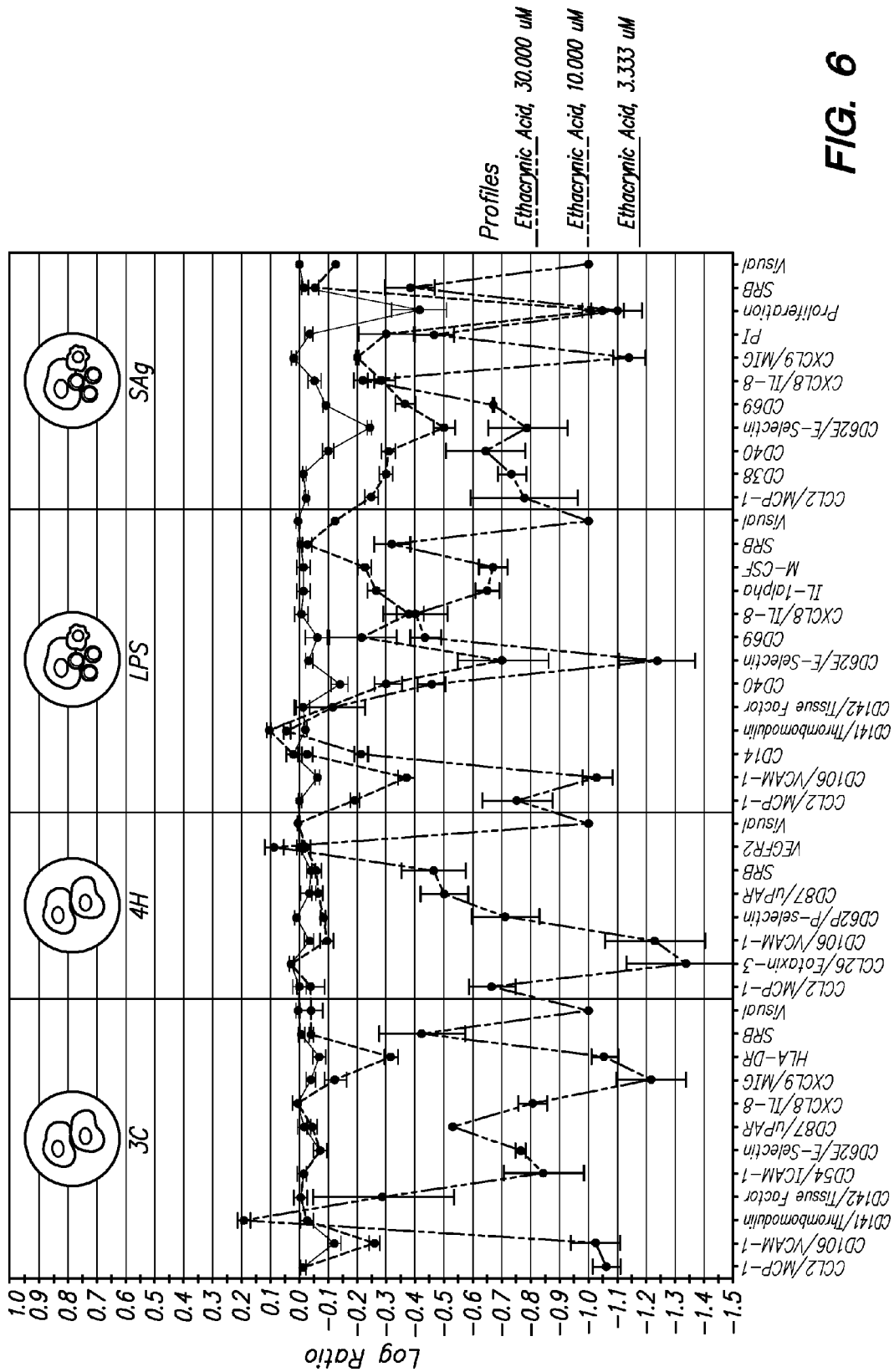

FIG. 6. BioMAP® profile of ethacrynic acid in BioMAP® systems of vascular inflammation. BioMAP® profile of ethacrynic acid shows a sharp dose-response. The profile at 30 μM shows toxicity to endothelial cells and PBMC in these systems. At 10 μM, the profile is similar to inhibitors of NFκB (FIG. 1) and shows BioMAP® features that are characteristic of NFκB inhibition including inhibition of VCAM, E-selectin and HLA-DR, T cell and monocyte activation and PBMC proliferation.

DETAILED DESCRIPTION OF EMBODIMENTS

The methods and compositions of the invention provide a system for the classification of biologically active agents according to toxicity, including determination of mechanism of toxicity; as well as assessment of candidate therapies for chemical warfare countermeasures, classification of toxic agents and countermeasures according to their mechanism of action, e.g. activation of cellular signaling pathways, and the like.

Datasets of information are obtained from biologically multiplexed activity profiling (BioMAP®) of agents that are potentially toxic, which agents include candidates for the treatment or involvement of chemical warfare agents; pharmaceutical drug candidates that may show toxic side effects; and the like. Such methods are described, for example, in U.S. Pat. No. 6,656,695 and U.S. Pat. No. 6,763,307; in co-pending U.S. patent application Ser. Nos. 10/220,999; 10/236,558; 10/716,349; and 10/856,564. Methods of analysis for such profiles are described in International application PCT/US2004/012688. Each of these documents are herein specifically incorporated by reference. Briefly, the methods provide screening assays for biologically active agents, where the effect of altering the environment of cells in culture is assessed by monitoring multiple output parameters. The result is a dataset that can be analyzed for the effect of an agent on a signaling pathway, for determining the pathways in which an agent acts, for grouping agents that act in a common pathway, for identifying interactions between pathways, and for ordering components of pathways.

Screening methods of interest utilize a systems approach to characterization of toxicity based on statistical analysis of protein expression data sets from multiple primary human cell-based systems. In these models, biological complexity is provided by the activation of multiple signaling pathways; interactions of multiple primary human cell types; and/or the use of multiple systems for data analysis. These model systems are surprisingly robust, reproducible, and responsive to and discriminatory of the activities of a large number of agents.

In order to analyze toxicity, and toxic countermeasures, systems may utilize combinations of cells that are informative of the poisoning processes, e.g. cellular models of vascular inflammation, monocyte/macrophage responses, T cell effector responses, fibrosis and skin biology, including novel systems modeling responses at epithelial surfaces, etc. are used. The multi-cell and/or multifactor design of the systems and their analysis through multi-parameter activity profiles work together to optimize information content, enabling rapid but effective analysis of drug and gene target activities in complex cellular responses relevant to clinical disease.

Cellular models selected for use in toxicity screening assays may be selected on the basis of various criteria. In such systems, the selection of readout parameters and conditions preferably allows enhanced discrimination of human cell states triggered by each of the known toxic agents tested; the system recapitulates known effects of agents on relevant cell types; and/or the system demonstrates cell-type specific pathway modulation. In the selection of individual parameters, usually a parameter will provide for a coefficient of variation (CV) of <10% for basal or stimulated expression using given detection technique; and/or $z^1$ values of >0.5 for the basal to stimulated expression window, or in the case of constitutively expressed readout parameters where $z^1$ values are not relevant, statistically significant modulation (p<0.05, across 3 or more experiments) by a test agent of interest (e.g. specific toxic agent, etc.) Criteria for multi-parameter profiles include significant modulation of 1 or more readout parameters (99% prediction envelope) by compounds from at least 3 different mechanism classes relevant to the model system; and reproducibility of profile shape (Pearson>0.7) across multiple repeats of the same compound on different days and ability to identify same compound in BLAST search of BioMAP® database with FDR<10%.

In one embodiment, the classification methods of the invention are used in automated informatics for the functional classification of chemical threat agents according to their biological activities in complex human cell systems and for definition of the induced pathways they target in order to better be able to identify effective countermeasures. This approach, which assesses the interaction of host pathways (e.g. inflammatory, etc.) with chemical-induced responses in an automated, high throughput format, provides an opportunity to identify novel countermeasures that would not be identified with current screening methods.

Pharmaceutical Agents

Agents of interest for analysis of toxicity by the methods of the invention and for incorporating in a reference database may include: approved and experimental human or animal pharmaceuticals. A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, nucleic acids, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Included are pharmacologically active drugs, genetic agents, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference.

In another embodiment, the invention is practiced by additionally examining the effect on these biological activities of known drugs and then selecting the agent(s) for stabilizing or preventing toxicity on the basis of their complementarity of action with those drugs.

Environmental Agents

Agents of interest for analysis by the methods of the invention and for incorporating in a reference database may include: pesticides, known toxic agents such as irritants, tumorigens, developmental and reproductive toxicants, neurotoxicants, immunotoxicants, nephrotoxicants, carcinogens, mutagens, teratogens and agents causing acute toxicity.

Chemical classes of particular interest may include: pyrethroids, conazoles, n-methyl carbamates, organophosphates, and perfluorinated compounds, polychlorinated biphenyls (PCB), fully halogenated chlorofluoroalkanes, dioxin, asbestos, and hexavalent chromium.

Test agents or samples of interest include, without limitation, prescription and non-prescription drugs, food additives, pesticides, fungicides, herbicides, solvents, diluents, chemical wastes, reaction products of chemical waste, and substances used in both industrial and household situations.

Cellular and metabolic poisons, which inhibit mitochondrial energy production, can affect a number of pathways, including cell survival and apoptosis pathways that are regulated by cell metabolic state. Although neurologic dysfunction is the most immediate symptom of metabolic poisoning, all cell types depend on metabolic energy and therefore can be affected by metabolic poisons. Lung injury and cardiovascular effects (including heart damage) can also result from metabolic poisoning. Metabolic poisons, which inhibit ATP production by interfering with mitochondrial electron transport chain Complex IV, can also inhibit the production of reactive oxygen species (ROS). ROS, by oxidation of signaling kinases, can regulate cell proliferation, cell survival and apoptosis pathways.

A variety of toxic chemical insults result in triggering of signals that initiate cell death. These agents can trigger apoptosis and necrosis pathways directly in exposed tissues. Cell death is a highly regulated cellular process that is coordinated, in part, by the mitochondria. Apoptosis or programmed cell death follows from triggering of certain cell surface receptors (death receptors) leading to activation of caspases which convey the apoptotic signal in a proteolytic cascade and induce mitochondrial dysfunction. Members of the BCL-2 family play a role in apoptosis by either protecting mitochondria (anti-apoptotic BCL-2 and BCL-XL) or inducing mitochondrial dysfunction (proapoptotic BAX, BID, BAD, etc.). Targeting of proapoptotic BCL-2 family members to the mitochondria causes alterations in the membrane potential, production of reactive oxygen species, opening of the permeability transition pore (PTP), and release of cytochrome c. The released cytochrome c activates Apaf-1, which in turn triggers a subsequent caspase cascade that then results in the degradation of cellular targets leading to cell death. Chemical insults that damage DNA can act through the cell cycle regulator, p53, and proapoptotic molecule BID, to cause leakage of cytochrome c and subsequent triggering of the caspase cascade. Severe insults, including genotoxic stimuli, result in necrosis, rather than apoptosis, if mitochondria are too severely damaged and become depleted of ATP (apoptosis requires ATP). PARP-1, a DNA repair enzyme that is induced by DNA damage, controls the transition of apoptosis to necrosis, in part, by depleting NAD+ and ATP from mitochondria if DNA damage is too severe.

Many cell signaling pathways contribute to the regulation of cell death. The anti-apoptotic BCL-2 and BCL-XL are stimulated by signaling through Erk and PKC, and inhibited by p53. The pro-apoptotic molecules BAD, BID and BAX are stimulated by signaling through JNK, p53, and GSK3β; and inhibited by signaling through AKT and PAK1/raf-1. The regulatory pathway controlling cell death can be complex. The AKT pathway, activated by growth factor signaling, can suppress apoptosis by phosphorylating and inactivating BAD, as well as GSK3β. The AKT pathway can also be regulated by necrosis. PARP-1 inhibitors have been shown to protect cells from oxidative stress induced cell death by stimulating the activation of PI-3 kinase/AKT pathway and preserving mitochondrial membrane potential. Understanding the regulation of cell death in settings relevant to tissue physiology will be important understanding the mechanisms of toxicity of environmental toxins.

Cytokines and lipid mediators also contribute to chemical agent toxicity by triggering the recruitment and activation of leukocytes, which leads to tissue damage if uncontrolled. The resulting injury is a consequence of a combination of direct effects of toxins and indirect effects of cytokines and/or factors. Proinflammatory cytokines, such as IL-1, TNF and IL-6, as well as arachidonic acid metabolites (TxA2, PGI2, etc.), regulate cell death. A full understanding of biologic response pathways to toxins must account for the complexity of these intracellular and intracellular signaling and regulatory pathways.

Both metabolic and endocrine systems are regulated by nuclear hormone receptor pathways, and a variety of environmental chemicals are known to target these receptors. The consequences of nuclear hormone receptor disruption include hormonal disturbances, metabolic disorders, and endocrine problems. Many nuclear hormone receptors are widely expressed (e.g. estrogen receptors, glucocorticoid receptors, PPARα, δ and γ receptors, etc.) and control gene expression and cell signaling pathways in multiple tissues.

Chemical Warfare Agents

Chemical warfare agents include poison gases and liquids, particularly those which are volatile, such as nerve gases, blistering agents (vesicants), and other extremely harmful or toxic chemicals. They are commonly dispersed as gases, smoke, or aerosols or by explosive means. As used herein, the term "chemical warfare agent" is intended to include those agents which are effective in relatively small dosages to substantially disable or kill mammals. Exemplary chemical warfare agents include choking agents, such as phosgene, chlorine, chloropicrin, diphosgene, etc.; blood agents, which act on the enzyme cytochrome oxidase, such as cyanogen chloride and hydrogen cyanide; incapacitating agents, such as 3-quinuclidinyl benzilate ("BZ"), vesicants, such as di(2-chloroethyl) sulfide (mustard gas or "HD") and dichloro(2-chlorovinyl)arsine (Lewisite); nerve agents, such as ethyl-N,N dimethyl phosphoramino cyanidate (Tabun or agent GA), o-ethyl-S-(2-diisopropyl aminoethyl) methyl phosphono-thiolate (agent VX), isopropyl methyl phosphonofluoridate (Sarin or Agent GB), methylphosphonofluoridic acid 1,2,2-trimethylpropyl ester (Soman or Agent GD).

Metabolic Poisons.

Cellular and metabolic poisons, such as cyanide, cyanogens chloride, hydrogen cyanide, inhibit mitochondrial energy production, and can affect a number of pathways, including cell survival and apoptosis pathways that are regulated by cell metabolic state (Dania) et al. (2004) Cell 116: 205-19). Although neurologic dysfunction is the most immediate symptom of cyanide poisoning, all cell types depend on metabolic energy and therefore can be affected by metabolic poisons. Lung injury and cardiovascular effects (including heart damage) can also result from cyanide poisoning. Cyanide, which inhibits ATP production by interfering with mitochondrial electron transport chain Complex IV, can also inhibit the production of reactive oxygen species (ROS). ROS, by oxidation of signaling kinases, can regulate cell proliferation, cell survival and apoptosis pathways.

Vesicants. Vesicants or blistering agents cause skin damage and respiratory distress by poorly defined, and possibly multiple, mechanisms. They can damage eyes, mucous membranes, respiratory tract, and internal organs. Agents include Lewisites (2-chlorovinyldichloroarsine (Lewisite 1); bis(2-chlorovinyl)chloroarsine (Lewisite 2); Tris(2-chlorovinyl)arsine (Lewisite 3), nitrogen mustards (Bis(2-chloroethyl)ethylamine (HN1); Bis(2-chloroethyl)methylamine (HN2); Tris (2-chloroethyl)amine (HN3)), mustard-lewisite, phosgene oxime, sulfur mustards (1,2-bis(2-chloroethylthio) ethane (Sesquimustard; Q); 1,3-Bis(2-chloroethylthio)-n-propane; 1,4-bis(2-chloroethylthio)-n-butane; 1,5-Bis(2-chloroethylthio)-n-pentane; 2-chloroethylchloromethylsulfide; bis(2-chloroethyl) sulfide (Mustard gas; HD); Bis(2-chloroethylthio) methane; bis(2-chloroethylthiomethyl)ether; Bis(2-chloroethylthioethyl)ether (O Mustard)); ethyldichloroarsine (a lewisite analog; ED); methyldichloroarsine (MD); phenyldichloroarsine (PD); and phosgene oxime (CX).

Toxicity mechanisms may involve DNA alkylation leading to metabolic effects, glutathione depletion, induction of free radical species, loss of calcium homeostasis, and/or arachidonic acid release. While sulfur mustard is rapidly metabolized following exposure, clinical effects can last days and weeks. Victim responses to sulfur mustard include cell death (in the skin, selective cell death of epidermal basal cell keratinocytes is a prominent feature) as well as inflammatory reactions such as vasodilation, increases in vascular permeability and leukocyte recruitment. Sulfur mustard has been shown to induce apoptosis and necrosis, potentially by interfering with AKT signaling (see Ray et al. (2005) Drug Chem. Toxicol. 28:105-16; Zhang et al. (2002) Br J. Pharmacol. 137:245-52). In cell culture, sulfur mustard treatment has been shown to increase the activity of the NFκB (nuclear factor kappa B) pathway and promote increased levels of TNFα, IL-8 and IL-6 expression in normal human keratinocytes. This increase in NFκB pathway activity may be related to inhibition of AKT, since the AKT pathway has been shown to suppress NFκB signaling.

Pulmonary agents impede a victim's ability to breathe, resulting in suffocation. These include adamsite (dm); acrolein; bis(chloromethyl)ether (bcme); chlorine ($Cl_2$); chloropicrin (ps); diphosgene (dp); methyl chlorosulfonate; phosgene (cg); and stannic chloride.

Nerve Agents.

Nerve agents are the most toxic chemical warfare agents. Many of these compounds are related to organophosphorus insecticides, in that they are both esters of phosphoric acid. The major nerve agents are diisopropylfluorophosphate (DFP), GA (tabun), GB (sarin), GD (soman), CF (cyelosarin), GE, CV, yE, VG (amiton), VM, VR (RVX or Russian VX), VS, and VX. Other chemical warfare agents of interest are Phosphonothioic acid, methyl-, S-(2-bis(1-methylethylamino)-ethyl) 0-ethyl ester O-ethyl; S-(2-diisopropylaminoethyl) methylphosphonothiolate; S-2-Diisopropylaminoethyl O-ethyl methylphosphonothioate; S-2((2-Diisopropylamino)ethyl) O-ethyl methylphosphonothiolate; O-ethyl S-(2-diisopropylaminoethyl) methylphosphonothioate; O-ethyl S-(2-diisopropylaminoethyl) methylthiolphosphonoate; S-(2-diisopropylaminoethyl) o-ethyl methyl phosphonothiolate; Ethyl-S-dimethylaminoethyl methylphosphonothiolate VX EA 1701; and TX60.

The nerve agents are classified into the C-series or V-series based upon their physical properties and toxicities. C-series nerve agents are volatile liquids at room temperature, and can be employed in liquid or vapor form. V series nerve agents, such as VX, are persistent liquid substances which can remain on material, equipment, and terrain for long periods. V-series nerve agents are generally more toxic than C-series nerve agents. Under temperate conditions, nerve agents are clear colorless liquids, which are difficult to detect.

The primary molecular target of nerve agents is acetylcholinesterase, inhibition of which results in high levels of acetylcholine. Because nerve agents may inhibit other enzymes and because the receptors for acetylcholine (muscarinic and nicotinic acetylcholine receptors) are widely expressed, these agents can impact a number of biological processes. Muscarinic receptors are G-coupled protein receptors that activate or regulate second messenger systems (phospholipase or adenylyl cyclase) whereas nicotinic receptors are ligand-activated ion channels. In addition to well known CNS effects, vascular and inflammatory effects of nerve agents include vasoconstriction, an increase in blood brain barrier permeability, as well as modulation of lymphocyte proliferation and cytokine production. Present treatment of organophosphate poisoning consists of post-exposure intravenous or intramuscular administration of various combinations of drugs, including carbamates (e.g., pyridostigmine), anti-muscarinics (e.g., atropine), and ChE-reactivators such pralidoxime chloride (2-PAM, Protopam). While these therapies are available, countermeasures that address the downstream mechanisms, and that might be appropriate for nerve agents that act with alternative mechanisms, e.g. where atropine is not effective, are of high interest.

Cell Death.

A variety of toxic chemical insults result in triggering of signals that initiate cell death. Cellular/metabolic poisons and blister agents trigger apoptosis and necrosis pathways directly in exposed tissues, and neuronal cell death is a feature of nerve agent intoxication. This point of convergence provides a common point for therapeutic intervention. Cell death is a highly regulated cellular process that is coordinated, in part, by the mitochondria. Apoptosis or programmed cell death follows from triggering of certain cell surface receptors (death receptors) leading to activation of caspases that convey the apoptotic signal in a proteolytic cascade and induce mitochondrial dysfunction. Members of the BCL-2 family play a role in apoptosis by either protecting mitochondria (anti-apoptotic BCL-2 and BCL-XL) or inducing mitochondrial dysfunction (proapoptotic BAX, BID, BAD, etc.). Targeting of proapoptotic BCL-2 family members to the mitochondria causes alterations in the membrane potential, production of reactive oxygen species, opening of the permeability transition pore (PTP), and release of cytochrome c. The released cytochrome c activates Apaf-1, which in turn triggers a subsequent caspase cascade that then results in the degradation of cellular targets leading to cell death. Chemical insults that damage DNA can act through the cell cycle regulator, p53, and proapoptotic molecule BID, to cause leakage of cytochrome c and subsequent triggering of the caspase cascade. Severe insults, including genotoxic stimuli, result in necrosis, rather than apoptosis, if mitochondria are too severely damaged and become depleted of ATP (apoptosis requires ATP). PARP-1, a DNA repair enzyme that is induced by DNA damage, controls the transition of apoptosis to necrosis, in part, by depleting NAD+ and ATP from mitochondria if DNA damage is too severe.

Many cell signaling pathways contribute to the regulation of cell death. The anti-apoptotic BCL-2 and BCL-XL are stimulated by signaling through Erk and PKC, and inhibited by p53. The pro-apoptotic molecules BAD, BID and BAX are stimulated by signaling through JNK, p53, and GSK3β; and inhibited by signaling through AKT and PAK1/raf-1. The regulatory pathway controlling cell death can be complex. The AKT pathway, activated by growth factor signaling, can suppress apoptosis by phosphorylating and inactivating BAD, as well as GSK3β. The AKT pathway can also be regulated by necrosis. PARP-1 inhibitors have been shown to protect cells from oxidative stress induced cell death by stimulating the activation of PI-3 kinase/AKT pathway and preserving mitochondrial membrane potential. Understanding the regulation of cell death in settings relevant to tissue physiology is important to the design and selection of agents that can protect cells from chemical threat agents.

Cytokines and lipid mediators also contribute to chemical agent toxicity by triggering the recruitment and activation of leukocytes, which leads to tissue damage if uncontrolled. The resulting injury is a consequence of a combination of direct effects of the chemical threat agents and indirect effects of cytokines and/or factors. Proinflammatory cytokines, such as IL-1, TNF and IL-6, as well as arachidonic acid metabolites (TxA2, PGI2, etc.), regulate cell death.

Biological Warfare Agents

Biowarfare (BW) threat agents including bacterial pathogens, hemorrhagic fever viruses, toxins, and bioregulators that subvert normal host processes by a variety of mechanisms. Despite the diversity of molecular mechanisms and seemingly inexhaustible numbers of potential or future threat agents (including novel genetically engineered forms), common themes emerge with respect to the host pathways and processes targeted by these agents. Inflammatory pathways are frequently impacted by BW threat agents, and are often critically involved in the most debilitating sequelae, including fever, cachexia, and, in the case of hemorrhagic fever viruses, lethal vasculopathy. BW counter-measures should include approaches that protect the targeted host pathways preferentially in a way that is independent of the threat agent itself, or that are broadly applicable to multiple agents. The development of these counter-measures will require (1) a broad-based technology for characterizing host responses to multiple, diverse BW threat agents (2) automated methodology for assigning pathways and networks targeted by multiple, diverse agents, and (3) a practical methodology for identifying broadly useful counter-measures. The ideal technology will be generally applicable to all known and future agents, and will encompass informatics-driven selection of optimal counter-measures based on automated analysis of the biological responses of human cell models.

Induction of inflammatory responses, including the production of proinflammatory cytokines and arachidonic acid metabolites, from various cell types, is a frequent consequence of exposure to a variety of BW agents including emerging threats, and contributes to much of the morbidity and lethality associated with exposure. Increased tumor necrosis factor-a (TNF), interleukins-1 and -6 (IL-1, IL-6) and prostaglandin 12 (PGI2) levels are found in patients with hemorrhagic fever viruses such as Dengue, Ebola and Hanta virus. Many bacterial pathogens, including the intracellular pathogens Listeria, Salmonella and Yersinia, as well as other Category A/B agents, make lipopolysaccharides (LPS) or other toxins that induce proinflammatory cytokine production. Recently, high levels of IFNγ and IP-10 were associated with fatal human influenza A subtype H5N1 disease. The host receptors that are targeted to trigger these pathogenic responses are diverse and include toll-like receptors, such as TLR2 and TLR4, T-cell receptors (TCR), and others.

Depending on the receptor or target distribution, proinflammatory cytokine production may be limited to particular cell types. For example, the receptor for Staphylococcal enteritis B toxin, TCRα/β, is restricted to T cells. In contrast, TL receptors and intracellular pathogenic targets are preferentially expressed in other cell types including monocytes and dendritic cells.

Proinflammatory cytokines, such as IL-1, TNF and IL-6, as well as arachidonic acid metabolites (TxA2, PGI2, etc.) bioregulators themselves, interfere with many vascular functions including the control of vessel constriction and vascular permeability. The resulting hypotension is a key component in shock. Cytokines and lipid mediators also play a key role in triggering the recruitment and activation of leukocytes, which, if uncontrolled, leads to tissue damage, and contributes to coagulopathy by altering the ability of the vasculature to regulate hemostasis. In some cases, the resulting vascular dysfunction is a consequence of a combination of direct effects of the BW agents themselves and indirect effects of host cytokines and factors. A full understanding of host pathogenesis response pathways must account for the complexity of pathway networks that are induced in vivo, including situations where multiple proinflammatory cytokines are present, or where pathways are altered by toxins.

Methods of Analysis

The data from a typical "system", as used herein, provides a single cell type or combination of cell types (where there are multiple cells present in a well) in an in vitro culture condition. Primary cells are preferred, or in the case of mast cells, cells derived from primary cells, to avoid potential artifacts introduced by cell lines. In a system, the culture conditions provide a common biologically relevant context. Each system comprises a control, e.g. the cells in the absence of the candidate biologically active agent, although usually in the presence of the factors in the biological context. The samples in a system are usually provided in triplicate, and may comprise one, two, three or more triplicate sets.

Systems of particular interest for toxic agent profiling include, without limitation, primary human endothelial cells, e.g. HUVEC, cultured in the presence of IL-1β+TNF-α+IFN-γ where parameters are selected from E-selectin, VCAM-1, ICAM-1, MCP-1, MIG, IL-8, HLA-DR, uPAR, CD141/thrombomodulin, CD142/Tissue Factor. Alternatively, endothelial cells may be cultured in the presence of IL-4 and histamine. Among the other factors useful for stimulating endothelial cells for these purposes are TNF-α; IL-1; IFNγ; thrombin; oxidized lipids; angiotensin-II; endothelin-1; aldosterone; IL-4; IL-13; TGFβ; histamine; glucose, insulin, etc., which may be used in combinations of one, two, three, four or more factors. Endothelial cells may also be used in a coculture with the cells listed below.

Multicellular systems of interest comprising peripheral blood mononuclear cells (PBMC; which are a mixture of CD4+ and CD8+T-cells, monocytes, NK cells, and other mononuclear leukocytes) and endothelial cells, where the T-cell receptor complex is stimulated with superantigen, or by stimulating toll receptor 4 (TLR4), e.g. with LPS. Parameters with the TLR4 system may be selected from CD14, CD142, CD40, CD69, MCP-1, E-selectin, IL-1α, IL-8, M-CSF, VCAM-1, CD25, thrombomodulin, and tissue factor. Parameters for the superantigen system may be selected from CD38, CD40, CD69, CD154/CD40L, E-selectin, IL-8, MCP-1, and MIG. T cells may be used instead of, or addition to, peripheral blood monocytes, including Th1 type T cells, regulatory T cells, etc. and particularly human T cells. T cell sources of interest include peripheral blood mononuclear cell preparations, which may be unselected, thereby providing a complex mixture of myeloid and lymphocytic cells, or may be selected for expression of T cell markers, such CD4+, CD3+, etc.

Primary human fibroblasts; early passage primary human keratinocytes; or a combination of the two are cultured with a combination of IL-1β, TNF-α, IFN-γ and/or TGFβ. Alternatively the cells are stimulated with TGFβ. Additional factors useful in this context are TNF-α; IFNβ; IFNγ; TGFβ; IL-4; IL-13; PDGF; FGF; histamine; etc. Macrophages and endothelial cells may be co-cultured with TLR2/6 ligand zymosan. Primary human bronchial epithelial cells may be stimulated with IL-1, TNF, IFNγ; or with TNF, IL4, IL-13. Smooth muscle cells, optionally co-cultured with endothelial cells, may be stimulated with IL-1β, TNF, and IFN-γ. Muscle cell sources of interest include human umbilical vein artery smooth muscle cells, primary aortic, bronchial, coronary or pulmonary artery smooth muscle cells. Other muscle cells of interest include skeletal muscle and cardiomyocytes, for example differentiated from bone marrow mesenchymal stem cells. Additional factors useful in this context are IFN-γ, IL-4, IL-1, TNF, thrombin, histamine, glucose, insulin, PDGF and TGF-β. Readout parameters for any of these systems include MCP-1 (monocyte chemoattractant protein-1), ICAM-1 (intracellular cell adhesion molecule-1), Collagen I, Collagen III, IP-10, Mig, M-CSF (macrophage colony stimulating factor), MMP-9, PAI-1, TGFβ1, TIMP-1, uPA, uPAR, I-TAC, HLA-DR, IL-1α, Keratin 8/18, MMP-1, Eotaxin-3, and IL-8.

In addition to cultures where pathways are activated, responses of resting cell systems provide additional power in detecting and discriminating the MoA and/or MoT of the induced biological responses. In such systems, the cells and parameters as described above are assessed, but the assay may be performed in the absence of cytokines or other pathway activators, with the exception of the toxic agents.

When a novel toxic agent modifies a unique combination of pathways not already in the database of bioactive agents, additional methods can be used to elucidate the key pathways involved. In this case, pathway involvement is assessed based on statistical analyses of pathway associations with particular parameter changes induced by the chemical agent. In BioMAP® systems, each parameter is regulated by multiple pathways. For each parameter that is modulated by a toxic agent, the overall BioMAP® reference database is searched (using the BioMAP® viewer) for pharmacologic or other bioactive agents that also modulate that parameter. Any reference compound or agent with known MoA can provide a MoA hypothesis as to the cellular pathway(s) affected by the chemical threat agent. If selected parameters in different BioMAP® systems are modified by known modulators of a given pathway, the level of confidence that the agent affects this pathway is increased. In the case where compounds are found with multiple different mechanisms, each inferred pathway can be tested.

As a general method to associate parameter changes with pathways, an algorithm is developed that will automatically generate specific hypotheses about the pathways implicated in the MoA/MoT of a given chemical threat agent based on the BioMAP® toxic profile that the agent elicits. The approach is loosely based on the lasso methodology described in Tibshirani (1996) J. Royal Statist. Soc. B., Vol. 58, No. 1, pp 267-288. In this approach, the problem is cast as one of regression in the form B=P*C where B is the BioMAP® toxic profile vector of agent-induced changes in each parameter, P is the matrix of a priori knowledge of parameter regulation by each of the many pathways modeled by the BioMAP® systems, and C is a vector of coefficients that represent the influence of a pathway on each parameter. P is 0, if a marker is not regulated, 1 if it is up regulated or −1 if it is down regulated by a given pathway. The coefficients C are determined from the solution of this regression equation. Because only a limited number of pathways will be affected by any specific agent, only a limited number of coefficients in C are expected to be non-zero.

Following this, in order to relax the constraints on the values of the matrix P (and not limit values to 0, 1 or −1) two alternative approaches are taken. The first approach is based on the solution obtained in the constrained case. Having determined the non-zero coefficients of the regression model, these coefficients are kept constant, and solve for the elements of matrix P. Alternatively, the influence of the chemical threat agents on the pathways can be modeled using a neural network approach. Connections between the pathways and the regulated markers are established based on prior knowledge of regulation but instead of modeling each output (BioMAP® toxic marker) as a linear combination of interacting pathways (the matrix P) non-linearity is introduced by allowing for the sum to be transformed through a nonlinear function $f(B_o + P*C)$. The "activation function" (f) is taken to be the logistic function similar to the approach used in neural networks. The solution for the weights (elements of vector C) is obtained by minimizing the sum of squares between the target values (BioMAP® toxic profile) and the output of the method for the corresponding marker. The use of the function $f$ provides an "activation" threshold mechanism and it is expected to better model the nonlinear interaction between pathways. The magnitude of the weights give the relative influence of each pathway to the observed marker value. Having obtained an initial solution for the weights (network corresponding to the a priori knowledge of regulation), an optimum network configuration that best explains the data by introducing a number of perturbations (for example by setting to zero coefficients that are small, effectively removing the connection between the pathway and the marker) is obtained. The outcomes of the two methodologies are compared and any discrepancies will resolved by alternative means.

Pathway predictions can be confirmed by selective pathway inhibitors (e.g. by testing if pharmacologic blockade of the predicted agent-activated pathways blunt the agent-induced BioMAP® toxic response). Alternatively, when the toxic agent is predicted to inhibit a cellular regulatory pathway, the prediction can be tested by pathway rescue by downstream products or overexpression of downstream pathway components. Gene over expression studies are performed, e.g. by retroviral gene transduction.

The BioMAP® toxic systems described above are applied to specific chemical threat agents and to identify effective countermeasures. To classify toxic agents, one or a panel of cellular systems as described above are contacted with an agent, usually duplicate samples are assayed. Control samples may include other agents with a known mechanism of action; negative controls in the absence of an agent; negative controls in the absence of pathways stimulators, e.g. cytokines, LPS, etc., and samples in the presence of a candidate countermeasure. Agents may be selected that affect a common pathway(s), as well as additional agent-specific pathways.

To classify toxic agent countermeasures, one or a panel of cellular systems as described above are contacted with an agent, usually duplicate samples are assayed. At least one sample there where the toxic agent is present may be provided. Control samples may include other agents with a known mechanism of action; negative controls in the absence of an agent; negative controls in the absence of pathways stimulators, e.g. cytokines, LPS, etc., and samples in the presence of a alternative toxic agents.

For countermeasures, a collection of candidate therapeutic agents can be screened using BioMAP® toxicity assay activities. Individual compounds may be identified that inhibit the pathological responses to a toxic agent, or a combination of 2 or 3 compounds may be identified to achieve an effective countermeasure.

Optimized assays to be employed for screening are chosen based on the BioMAP® toxic data and analyses of chemical threat agent profiles. A combination of assays and parameters will be selected to maximize the probability of identifying new compounds that reverse agent effects, minimizing false negatives. False positives can be quickly eliminated using secondary screening. Information theory-based algorithms will be applied to identify reduced parameter/assay sets that retain sensitivity to all known agent-induced response pathways (but may not discriminate pathways in the primary screen).

Selected compounds can be confirmed by testing in additional BioMAP® systems and comparison with known approved and experimental therapeutics. If indicated, pathway mechanisms can be confirmed by biochemical techniques.

In one embodiment of the invention, a candidate agent is assayed in one or more, two or more, three or more, four or more of the assays set forth in Table 1, and the changes in parameter readouts collected in a dataset after normalization, averaging, etc. as described herein. Compounds that provide for a predetermined number of changes are identified as having a particular mechanism of toxicity.

As used herein, the biological context refers to the exogenous factors added to the culture, which factors stimulate pathways in the cells. Numerous factors are known that induce pathways in responsive cells. By using a combination of factors to provoke a cellular response, one can investigate multiple individual cellular physiological pathways and simulate the physiological response to a change in environment.

A BioMAP® dataset comprises values obtained by measuring parameters or markers of the cells in a system. Each dataset will therefore comprise parameter output from a defined cell type(s) and biological context, and will include a system control. As described above, each sample, e.g. candidate countermeasure agent, toxic agent, etc., will generally have triplicate data points; and may be multiple triplicate sets. Datasets from multiple systems may be concatenated to enhance sensitivity, as relationships in pathways are strongly context-dependent. It is found that concatenating multiple datasets by simultaneous analysis of 2, 3, 4 or more systems will provide for enhance sensitivity of the analysis.

By referring to a BioMAP® is intended that the dataset will comprise values of the levels of at least two sets of parameters, preferably at least three parameters, more preferably 4 parameters, and may comprise five, six or more parameters.

In many cases the literature has sufficient information to establish the system conditions to provide a useful BioMAP®. Where the information is not available, by using the procedures described in the literature for identifying markers for diseases, using subtraction libraries, microarrays for RNA transcription comparisons, proteomic or immunologic comparisons, between normal and cells in the physiologic state of interest, using knock-out and knock-in animal models, using model animals that simulate the physiological state, by introducing cells or tissue from one species into a different species that can accept the foreign cells or tissue, e.g. immunocompromised host, one can ascertain the endogenous factors associated with the physiologic state and the markers that are produced by the cells associated with the physiologic state.

The parameters may be optimized by obtaining a system dataset, and using pattern recognition algorithms and statistical analyses to compare and contrast different parameter sets. Parameters are selected that provide a dataset that discriminates between changes in the environment of the cell culture known to have different modes of action, i.e. the BioMAP® is similar for agents with a common mode of action, and different for agents with a different mode of action. The optimization process allows the identification and selection of a minimal set of parameters, each of which provides a robust readout, and that together provide a BioMAP® that enables discrimination of different modes of action of stimuli or agents. The iterative process focuses on optimizing the assay combinations and readout parameters to maximize efficiency and the number of signaling pathways and/or functionally different cell states produced in the assay configurations that can be identified and distinguished, while at the same time minimizing the number of parameters or assay combinations required for such discrimination. Optimal parameters are robust and reproducible and selected by their regulation by individual factors and combinations of factors.

Parameters are quantifiable components of cells. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc.

Markers are selected to serve as parameters based on the following criteria, where any parameter need not have all of the criteria: the parameter is modulated in the physiological condition that one is simulating with the assay combination; the parameter has a robust response that can be easily detected and differentiated; the parameter is not co-regulated with another parameter, so as to be redundant in the information provided; and in some instances, changes in the parameter are indicative of toxicity leading to cell death. The set of parameters selected is sufficiently large to allow distinction between datasets, while sufficiently selective to fulfill computational requirements.

Parameters of interest include detection of cytoplasmic, cell surface or secreted biomolecules, frequently biopolymers, e.g. polypeptides, polysaccharides, polynucleotides, lipids, etc. Cell surface and secreted molecules are a preferred parameter type as these mediate cell communication and cell effector responses and can be readily assayed. In one embodiment, parameters include specific epitopes. Epitopes are frequently identified using specific monoclonal antibodies or receptor probes. In some cases the molecular entities comprising the epitope are from two or more substances and comprise a defined structure; examples include combinatorially determined epitopes associated with heterodimeric integrins. A parameter may be detection of a specifically modified protein or oligosaccharide, e.g. a phosphorylated protein, such as a STAT transcriptional protein; or sulfated oligosaccharide, or such as the carbohydrate structure Sialyl Lewis x, a selectin ligand. The presence of the active conformation of a receptor may comprise one parameter while an inactive conformation of a receptor may comprise another, e.g. the active and inactive forms of heterodimeric integrin □M□2 or Mac-1.

Parameters of interest for the evaluation of toxic agents include, without limitation, MCP-1, Collagen I, VCAM-1, CD40, IP-10, MIG, M-CSF, PAI-1, ICAM-1, CD90, IL-8, Eotaxin-3, Collagen III, CD36, CD163, Mac-1, endothelin-1, E-selectin, Thrombomodulin, Tissue Factor, uPAR, HLA-DR, MIP-1alpha, MIP-3alpha, MDC, MMP-13, transferrin, LDL-R, M-CSF, CD38, CD69, CD25, IFN-γ, IL-1, IL-6, histamine, TNF-α, leptin, CRP, GLT4, resistin, TNFRI, TNFRII, creatine kinase, serum amyloid A, LOX-1, adiponectin, glucose, resistin, pentraxin-3, tryptase, VEGF, PDGF, TGFβR. Hepatocyte GF, P-selectin, vWF, fibrinogen, HDL, LDL, apolipoproteins, IL-11, IL-23, TGFb, MMP-1, MMP-2, MMP-9, MMP-11, TIMP-1, TIMP-2, IGF-1, EGF, VEGFR2, tPA, uPA, ITAC, C5a, C3a, PGI2, TXA2, ACE, AT2R1, angiotensin II, ANP, and nitric oxide. Other parameters of interest include arachidonic acid metabolites, such as prostaglandins, PGE2, PGI2, 15δ-PGJ2, 6keto-PGF1α, PGF2α, and leukotrienes such as Cysteinal leukotriene and LTB4.

Candidate countermeasure agents may encompass numerous chemical classes, primarily organic molecules, which may include organometallic molecules, inorganic molecules, genetic sequences, etc. An important aspect of the invention is to evaluate candidate countermeasure agents with preferred biological response functions, e.g. broad activity against multiple toxic agents in a class. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Countermeasure agents include, without limitation, anti-inflammatory drugs, anti-cholinesterase, protease inhibitors, and inhibitors of PARP-1. Anti-inflammatory drugs, analogs and derivatives thereof, or other modulators of inflammation may include, without limitation: histamine agonists, e.g. histamine, betazole, impromidine; histamine antagonists including H1 selective, H2 selective and non-selective blockers, e.g. doxylamine clemastine, brompheniramine triprolidine, cimetidine, chlorpheniramine, famotidine, diphenhydramine, nizatidine, promethazine, ranitidine, loratidine, levocobastine, cetirizine, acravastine; inhibitors of histamine release, e.g. cromalyn, nedocromil, eicosanoids. Leukotriene antagonists may include zafirlakast; inhibitors of leukotriene synthesis may include zileuton, montelekast, carboprost, dinoprotone, alprostadil, dinoprost, and misoprostol. Kinin modulators include bradykinin and aprotinin. NSAIDs, acetaminophen, aspirin and related salicylates are all of interest. Such drugs may include, without limitation, aspirin and salicylates, meclofenamate, celecoxib, diclofenac sodium, naproxen, rofecoxib, fenoprofen, phenylbutazone, meloxicam, ibuprofen, piroxicam, namebutone, indomethacin, sulindac, ketoprofen, and tometin. Immunosuppressants and anti-proliferatives include rapamycin, methotrexate, azathioprine, cyclosporin, FK-506, cdk inhibitors, and corticosteroids.

The term "genetic agent" refers to polynucleotides and analogs thereof, which agents are tested in the screening assays of the invention by addition of the genetic agent to a cell. Genetic agents may be used as a factor, e.g. where the agent provides for expression of a factor. Genetic agents may also be screened, in a manner analogous to chemical agents. The introduction of the genetic agent results in an alteration of the total genetic composition of the cell. Genetic agents such as DNA can result in an experimentally introduced change in the genome of a cell, generally through the integration of the sequence into a chromosome. Genetic changes can also be transient, where the exogenous sequence is not integrated but is maintained as an episomal agent. Genetic agents, such as antisense oligonucleotides, can also affect the expression of proteins without changing the cell's genotype, by interfering with the transcription or translation of mRNA. The effect of a genetic agent is to increase or decrease expression of one or more gene products in the cell.

Agents are screened for biological activity by adding the agent to cells in the system; and may be added to cells in multiple systems. The change in parameter readout in response to the agent is measured to provide the BioMAP® dataset.

The data, particularly data from multiple toxic relevant systems, may be subjected to non-supervised hierarchical clustering to reveal relationships among profiles. For example, hierarchical clustering may be performed, where the Pearson correlation is employed as the clustering metric. Clustering of the correlation matrix, e.g. using multidimensional scaling, enhances the visualization of functional homology similarities and dissimilarities. Multidimensional scaling (MDS) can be applied in one, two or three dimensions. Application of MDS produces a unique ordering for the agents, based on the distance of the agent profiles on a line. To allow objective evaluation of the significance of all relationships between compound activities, profile data from all multiple systems may be concatenated; and the multi-system data compared to each other by pairwise Pearson correlation. The relationships implied by these correlations may then be visualized by using multidimensional scaling to represent them in two or three dimensions.

Biological datasets are analyzed to determine statistically significant matches between datasets, usually between test datasets and control, or profile datasets. Comparisons may be made between two or more datasets, where a typical dataset comprises readouts from multiple cellular parameters resulting from exposure of cells to biological factors in the absence or presence of a candidate agent, where the agent may be a toxic agent, a toxic agent countermeasure, etc.

A prediction envelope is generated from the repeats of the control profiles; which prediction envelope provides upper and lower limits for experimental variation in parameter values. The prediction envelope(s) may be stored in a computer database for retrieval by a user, e.g. in a comparison with a test dataset.

In one embodiment of the invention, the analysis methods provided herein are used in the determination of functional homology between two agents. As used herein, the term "functional homology" refers to determination of a similarity of function between two candidate agents, e.g. where the agents act on the same target protein, or affect the same pathway. Such analysis is of particular interest for determining functional homology between toxic agents, which information is useful in the classification of agents for countermeasures. Similarly, functional homology between countermeasure agents is of interest for determining classes of agents with a similar mechanism of action, in order to appropriately treat victims of toxic agents.

Functional homology may also distinguish compounds by the effect on secondary pathways, i.e. side effects. In this manner, compounds or genes that are structurally dissimilar may be related with respect to their physiological function. Parallel analyses allow identification of compounds with statistically similar functions across systems tested, demonstrating related pathway or molecular targets. Multi-system analysis can also reveal similarity of functional responses induced by mechanistically distinct drugs.

EXAMPLES

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade; and pressure is at or near atmospheric.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. It is particularly to be understood that the present invention is not limited to the particular embodiments described herein. For example, the invention is not restricted to the particular methodology, protocols, cell lines, animal species or genera, constructs and reagents described herein as such may vary. The foregoing has been merely a description of certain preferred embodiments of the invention, not intended to limit the scope of that invention, which is defined only by the appended claims.

Example 1

BioMAP® Systems.

BioMAP® systems biology technology has been used for characterizing and classifying drugs and other bioactive agents based on the functional activities of a panel of complex primary human cell-based assays revealed by statistical analysis of protein levels measurements. In each assay system, different primary human cell types (either as monoculture or as a co-culture of a mixture of cell types) are stimulated with a combination of biological mediators (growth factors, cytokines, etc., as input factors) and the levels of a panel of readout measurements (proteins, etc.) are measured with and without test agent (chemical threat agent, compound, drug). Table 1 shows a number of established BioMAP® systems that represent the biology of immune responses, vascular biology, inflammation, lung, skin and tissue biology. In these assays, primary human cells, peripheral blood mononuclear cells co-cultures or other co-cultures are activated in complex environments. These assays have been optimized for automation (microplate formats), and have been used to test a large number of drugs and other bioactive agents.

TABLE 1

Cell types, input stimuli of BioMAP® systems.

| Cell Types | Environment | Readout Parameters |
|---|---|---|
| Endothelial cells | IL-1β + TNF-α + IFN-γ | E-selectin, VCAM-1, ICAM-1, MCP-1, MIG, IL-8, HLA-DR, uPAR, Thrombomodulin, Tissue Factor, Proliferation, SRB, Visual |
| Endothelial cells | IL-4 + histamine | VEGFRII, P-selectin, VCAM-1, uPAR, Eotaxin-3, MCP-1, SRB, Visual |
| Peripheral blood mononuclear cells + Endothelial cells | TLR4 | CD40, CD69, MCP-1, E-selectin, IL-1α, IL-8, M-CSF, VCAM-1, Thrombomodulin, Tissue Factor, TNF-α, PGE$_2$, SRB, Visual |
| Peripheral blood mononuclear cells + Endothelial cells | TCR | CD38, CD40, CD69, E-selectin, IL-8, MCP-1, MIG, PI, SRB, Visual, Proliferation |
| Peripheral blood mononuclear cells + Endothelial cells | None | CD40, CD69, MCP-1, E-selectin, IL-8, M-CSF, VCAM-1, Thrombomodulin, Tissue Factor, TNF-α, PGE$_2$, CD38, MIG, SRB, Visual |
| Bronchial epithelial cells | IL-1β + TNF-α + IFN-γ | ICAM-1, uPAR, IP-10, I-TAC, MIG, HLA-DR, IL-1α, Keratin 8/18, MMP-1, MMP-9, PAI-1, SRB, tPA, uPA, IL-8, EGFR, TGF-β1, Visual |
| Bronchial epithelial cells | TNF-α + IL-4 | Eotaxin-3, ICAM-1, IL-8, IL-1α, Keratin 8/18, MMP-9, PAI-1, tPA, TGF-β1, uPA, EGFR, Collagen I, SRB, Visual |
| Bronchial epithelial cells | None | ICAM-1, uPAR, IP-10, I-TAC, MIG, HLA-DR, Eotaxin-3, IL-1α, Keratin 8/18, MMP-1, MMP-9, PAI-1, SRB, tPA, uPA, IL-8, EGFR, TGF-β1, Visual |
| Bronchial epithelial cells + Fibroblasts | TNF-α + IL-4 | MCP-1, Eotaxin-3, VCAM-1, ICAM-1, IL-8, Keratin 8/18, MMP-1, MMP-9, uPA, tPA, MMP-3, CD90, PAI-1, IL-1α, TGF-β1, SRB, Visual |
| Fibroblasts | IL-1β + TNF-α + IFN-γ + TGF-β | MCP-1, Collagen 1, VCAM-1, IP-10, MIG, M-CSF, PAI-1, ICAM-1, IL-8, MMP-1, TIMP-2, SRB, Visual |
| Fibroblasts | TGF-β | Collagen I, Collagen III, PAI-1, TIMP-1, TIMP-2, SRB, Visual |
| Fibroblasts | IL-1β + TGF-βIFN-γ | MCP-1, VCAM-1, ICAM-1, IP-10, IL-8, MIG, Collagen I, Collagen III, EGFR, I-TAC, M-CSF, MMP-1, PAI-1, Proliferation, TIMP-1, TIMP-2, TGF-β1, SRB, Visual |
| Fibroblasts | IL-1β + TNF-α + IFN-γ + bFGF + EGF + PDGF-BB | MCP-1, VCAM-1, ICAM-1, IP-10, IL-8, MIG, Collagen I, Collagen III, EGFR, I-TAC, M-CSF, MMP-1, PAI-1, Proliferation, TIMP-1, TIMP-2, TGF-β1, SRB, Visual |
| Fibroblasts | None | MCP-1, VCAM-1, ICAM-1, IP-10, IL-8, MIG, Collagen I, Collagen III, EGFR, I-TAC, M-CSF, MMP-1, PAI-1, Proliferation, TIMP-1, TIMP-2, TGF-β1, SRB, Visual |
| Lung Myofibroblasts | TNF-α + TGF-β | Collagen I, Collagen III, Collagen IV, Decorin, a-Smooth Actin, bFGF, TIMP-1, TIMP-2, SRB, MMP-1, PAI-1, MMP-3, Visual |
| Keratinocytes | IL-1β + TNF-α + IFN-γ + TGF-β | ICAM-1, IP-10, MIG, IL-1α, MMP-9, PAI-1, TGF-β1, TIMP-2, uPA, SRB, Visual |
| Keratinocytes + Fibroblasts | None | MCP-1, VCAM-1, ICAM-1, IL-8, IP-10, MIG, IL-1α, MMP-9, TGF-β1, Collagen I, Collagen III, I-TAC, M-CSF, MMP-1, TIMP-2, uPA, SRB, Visual |
| Keratinocytes + Fibroblasts | IL-1β + TNF-α + IFN-γ + TGF-β | MCP-1, ICAM-1, IP-10, MIG, IL-1α, MMP-9, TGF-β1, TIMP-2, uPA, SRB, Visual |
| Endothelial cells + Mast cells | IL-4 + anti-IgE | Eotaxin-3, VCAM-1, ICAM-1, P-selectin, uPAr, IL-8, Endothelin-1, PAI-1, Mast Cell Tryptase, SRB, Visual |

TABLE 1-continued

Cell types, input stimuli of BioMAP ® systems.

| Cell Types | Environment | Readout Parameters |
|---|---|---|
| Endothelial cells + M1 macrophages | TLR2 (low hydrocortisone) | MCP-1, MIP-1α, VCAM-1, CD40, E-selectin, CD69, IL-8, IL-1α, M-CSF, SRB, SRB-Mphg, Visual |
| Endothelial cells + Vascular smooth muscle cells | IL-1β + TNF-α + IFN-γ | MCP-1, VCAM-1, Thrombomodulin, Tissue Factor, CD40, E-selectin, uPAR, IL-8, MIG, Endothelin-1, HLA-DR, LDLR, M-CSF, SAA, SRB, Visual |
| Vascular smooth muscle cells | IL-1β + TNF-α + IFN-γ | MCP-1, VCAM-1, Thrombomodulin, Tissue Factor, uPAR, IL-8, MIG, HLA-DR, IL-6, LDLR, M-CSF, SAA, SRB, Visual |
| Vascular smooth muscle cells | IL-1β + TNF-α + IFN-γ | MCP-1, VCAM-1, Thrombomodulin, Tissue Factor, uPAR, IL-8, MIG, HLA-DR, IL-6, LDLR, M-CSF, SAA, SRB, Visual |
| Endothelial cells + $T_H2$ blasts | TCR + IL-2 | MCP-1, Eotaxin-3, VCAM-1, CD38, CD40, E-selectin, P-selectin, CD69, uPAR, IL-8, MIG, SRB, PI, Visual |

BioMAP® Profiles.

Figure 1:
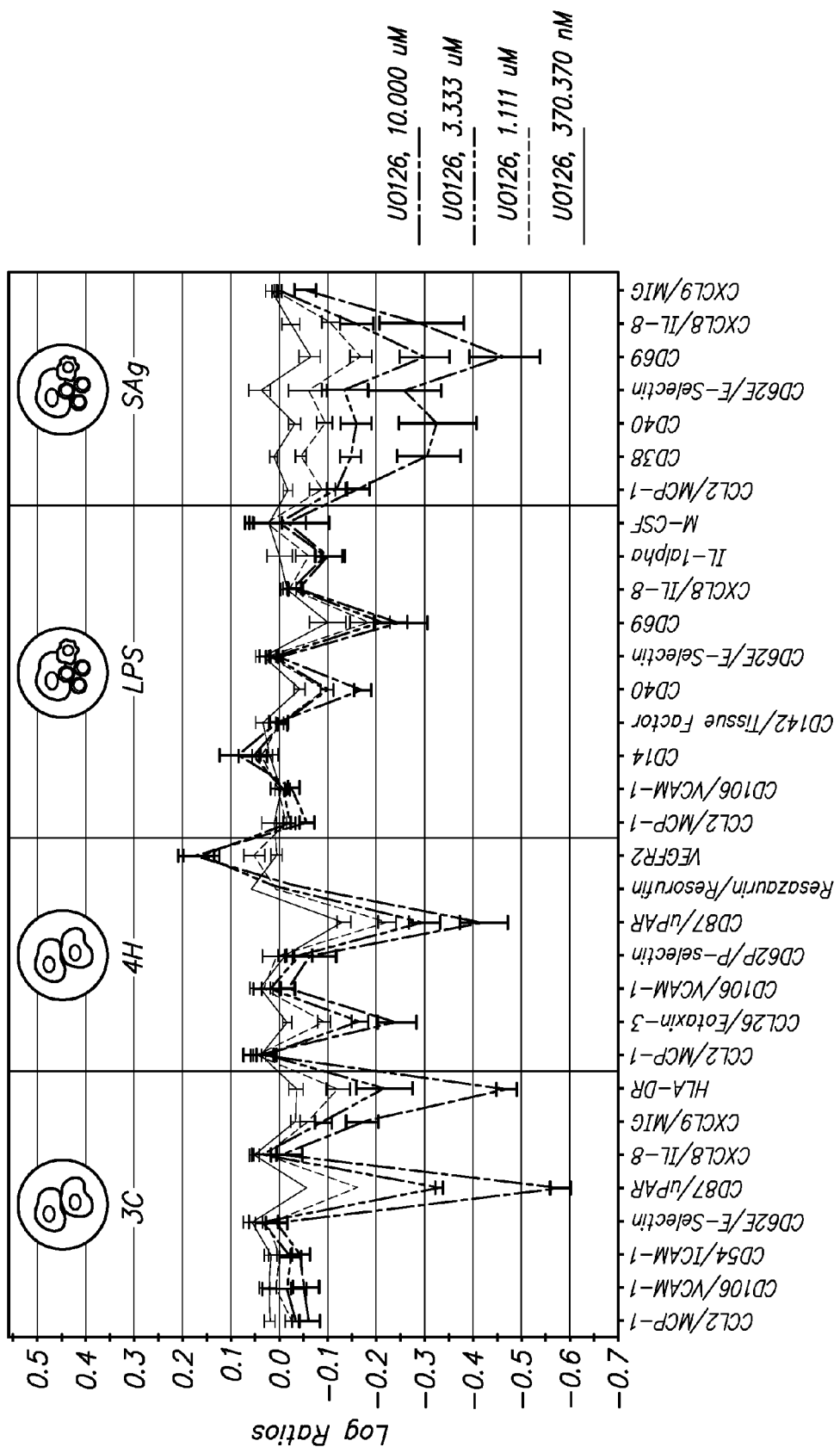
FIG. 1. BioMAP® Activity profile for UO126, an experimental MEK kinase inhibitor. Activity profile for UO126, an experimental MEK kinase inhibitor on selected protein readouts in 4 systems (left, BioMAP® systems 1, 4, 2 and 3 from Table 1). Protein readouts are listed on the x-axis and the y-axis shows Log 10 expression ratios of the relative levels of the protein readouts measured with versus without drug. Grey box indicates the 99% confidence envelope (based on buffer controls). Data are from at least 3 separate experiments (each experiment in triplicate). The function similarity map (right) is generated from analysis of BioMAP® profiles of 46 mechanistically diverse compounds (colored according to MoA).

Depending on the mechanism of action (MoA), drugs (or other bioactive agents) induce specific changes in the expression levels of protein readouts, giving a specific BioMAP® profile. A BioMAP® profile generated for the experimental MEK kinase inhibitor, UO126, in four BioMAP® systems is shown in FIG. 1. We have evaluated the influence of cell donor, passage number, and experimental sources of variability on readout protein measurements, and developed methods for managing variability to generate statistically robust BioMAP® activity datasets have been previously described. Robust procedures for managing assay performance, QA/QC metrics, etc. have been implemented. The CV's for readout parameters range from 7-14%.

BioMAP® Databases.

For managing assays and raw assay data from BioMAP® profiling CambridgeSoft's BioAssay HTS is used, and a proprietary JAVA-based application (BioMAPViewer™) that retrieves and visualizes profile data. Analysis tools for calculating various statistics, generating pair-wise correlation analyses (using a variety of similarity metrics), hierarchical trees, and building 2D and 3D networks using multi-dimensional scaling, have also been developed and integrated into BioMAPViewer™. BioMAP® Viewer also contains an information management system), which connects BioMAP® profile data with information from public databases and the literature, as well as other data types. Currently the BioMAP® database contains thousands of BioMAP® profiles from a large and diverse set of compounds including approved therapeutics (inflammation, cancer, metabolism and cardiovascular disease), experimental compounds, toxic agents, natural products and biologics.

Data Analysis.

Mean values for each parameter measured (e.g. by ELISA, etc.) are calculated from replicate samples per experiment, and are then used to generate ratios between treated (e.g. drug, etc.) and matched control (e.g. media or DMSO) parameter values within each experiment. The significance of changes in individual parameter readouts is assessed by measuring the variance of replicate control samples, and generating a confidence interval from the empirical data (e.g. 95% interval contains 95% of all control values, etc.). The normalized parameter ratios are then log 10 transformed and, for example, used in correlation calculations.

As shown in FIG. 1, while the magnitude of changes in the levels of readout parameters varies according to dose, the overall shape of the profile does not. Thus, similarity metrics that depend on shape, such as Pearson's correlation coefficient, are effective in correctly classifying drugs (and agents) with the same target mechanism. Significant correlations of multi-parameter data sets can be determined by 1) creating a distribution of Pearson correlations using randomized data made from permuting the empirical profiles, 2) selecting a Pearson correlation to minimize the False Discovery Rate (FDR). The FDR is the ratio of the number of correlations greater than the selected Pearson correlation in the randomized data to the number of correlations greater than the selected Pearson correlation in the empirical data, and 3) applying this cut-off Pearson correlation value to the correlations between experimental profiles. This ensures that for a 5% FDR, 95% of the correlations derived from the experimental profiles are a result of a true biological effect, and not random chance.

Correlations can then be visualized in two dimensions by multidimensional scaling. These compound relationships may be visualized by multi-dimensional scaling and illustrates how compounds with the same color-coded target mechanisms elicit significantly similar profiles (connected by lines, for example in FIG. 3).

Mechanism of Action.

Comparing BioMAP® profiles generated for novel drugs and agents to the BioMAP® reference database (>6000 BioMAP® activity profiles), is effective at revealing MoA. When a search of the database for compounds with BioMAP® profiles similar to PD169316, a p38 kinase inhibitor) is performed, the top 20+ matches returned from database are all other inhibitors of p38 kinase. A large number of target mechanisms are detected and distinguished by BioMAP® analysis including many kinase targets (PI-3 kinase, Jak, Ick, PKA, PKC, IKK2, MEK, p38, JNK, etc.), nuclear hormone receptors (PPARγ, RAR/RXR), non-kinase enzymes (phosphatases, dehydrogenases, HMG-CoA reductase (3-hydroxy-3-methyl-glutaryl-CoA reductase), HDAC (histone deacetylase), ACE (angiotensin converting enzyme, GPCRs (PAFR, platelet activating factor, histamine, β-adrenergic) and ion channels (L-type calcium channels). In some cases, compounds inhibiting the same target do not elicit similar BioMAP® profiles and do not cluster in this analysis. Differences can then be attributed to secondary or off target effects.

In addition to target mechanisms, pathway relationships can also be derived from analysis of BioMAP® data. In one approach, genes encoding individual signaling pathway components have been over expressed in primary human endothelial cells, and effects on cell responses combined to comprise BioMAP® profiles, which are then compared for similarity. BioMAP® profiles generated by components of the NF-κB pathway, RasMAPK, PI-3 kinase/AKT and Interferon-γ pathways cluster according to their pathways. Components that mediate pathway cross talk, such as IRAK and MyD88 are revealed by this analysis. These pathways have been implicated in biologic responses to chemical agents. In a second approach, pathway relationships are identified by using pharmacologic inhibitors. For example, the similarity between inhibitors of PI-3 kinase (LY294002 and Wortmannin) and mTOR (mammalian target of rapamycin) is consistent with mTOR's location just downstream of PI-3 kinase); and similarity between inhibitors of IκBα and IKK-2 is consistent with their involvement in the NE-κB pathway. A third approach builds on the information from pharmacologic inhibitors to categorize pathway regulation of individual parameters. From pharmacologic inhibitor (and activator) data, the pathways regulating parameters in the 3 cytokine (3C) BioMAP® system, which stimulates a chronically inflamed endothelium have been identified (Table 2).

ing to select effective countermeasures based on agent activities and/or pathways modulated.

Forty compounds, including examples of known CW or toxic agents as well as reference compounds, are profiled in BioMAP® assays covering the biology of vascular inflammation, monocyte/macrophage responses, T cell effector responses, fibrosis and skin biology.

TABLE 2

Pathways regulating parameters in the 3C BioMAP ® system.

| Parameter | MCP-1 | Tissue Factor | VCAM-1 | ICAM-1 | E-selectin | IL-8 | MIG | HLA-DR |
|---|---|---|---|---|---|---|---|---|
| PATHWAYS | hsp90 | Jak/Stat | NFκB | hsp90 | Adenylate cyclase | Adenylate cyclase | Jak/Stat | hsp90 |
|  | Guanine synthesis | NFκB | Ras/MAPK | NFκB | Cholesterol synthesis | hsp90 | NFκB | Jak/Stat |
|  |  | PI-3 kinase |  |  | hsp90 | NFκB | PKC | NFκB |
|  |  | PKC |  |  | Jak/Stat | RAR/RXR |  | PI-3 kinase |
|  |  | VEGFR |  |  | NFκB |  |  | p38 kinase |
|  |  |  |  |  | PKA |  |  | RAR/RXR |
|  |  |  |  |  | PKC |  |  |  |

Figure 2:
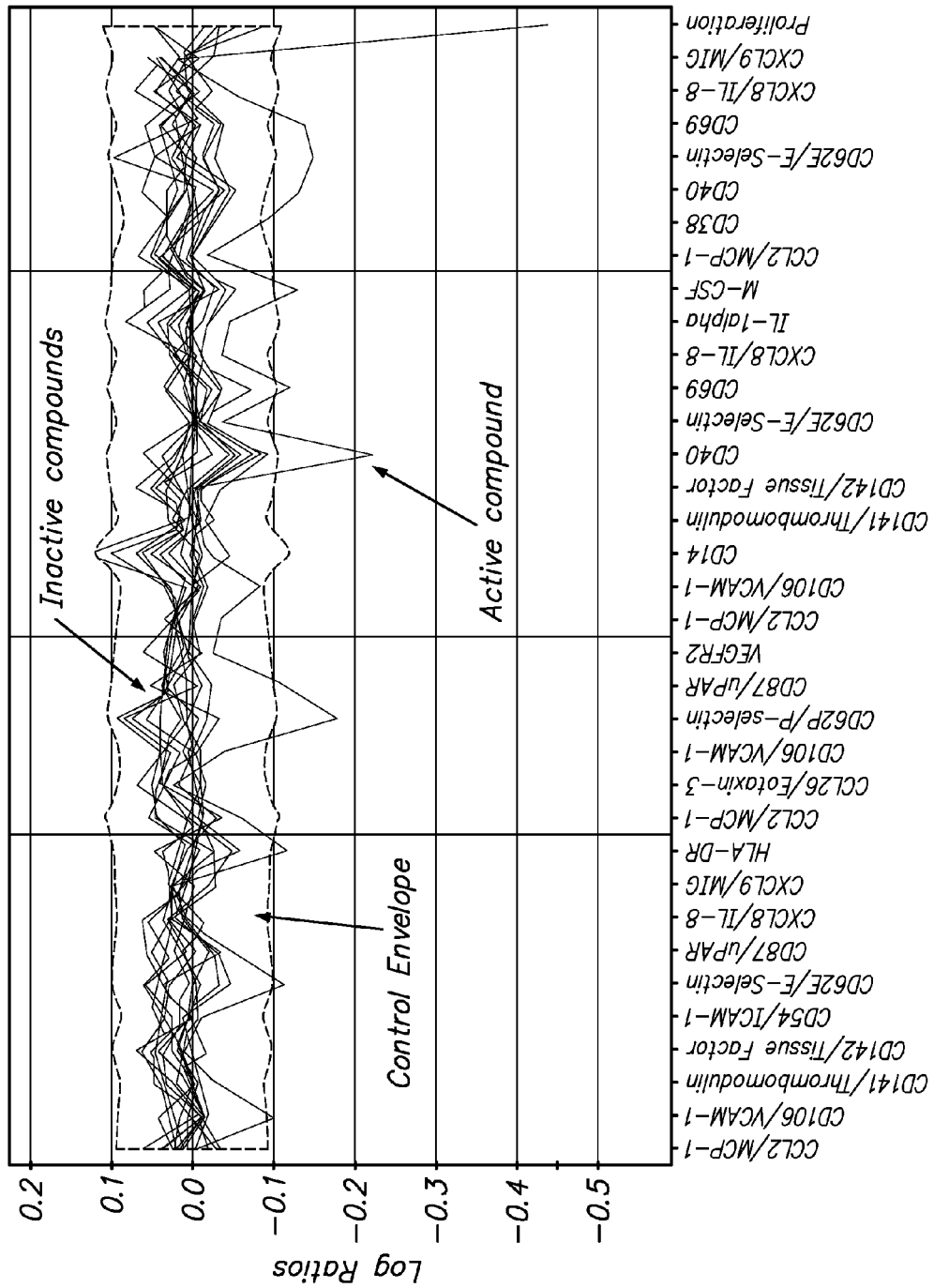
FIG. 2. BioMAP® activity profiles for compounds from diverse chemical classes screened for anti-inflammatory activities. The active compound shown alters the levels of several assay endpoints, to a significant degree with values falling outside the control envelope.

FIG. 2 shows an overlay of BioMAP® profiles of compounds screened in 4 BioMAP® model systems. Compounds were tested at 3-10 μM. One active compound, BSK-1345, that modulates several BioMAP® parameters outside the confidence envelope (grey) is indicated (dark purple). The active compound shown was confirmed in follow up studies and tested in animal models.

For toxic agents, assay systems that can assess biologic responses by epithelial cells are important, as these are relevant to sites of initial exposure. BioMAP® assays using primary human keratinocytes, bronchial epithelial cells, and fibroblast-epithelial cell co-cultures, relevant to inflammatory settings are useful in this respect. Methods for culturing these cells and optimal assay formats have been developed.

BioMAP® systems are applied to screening of small compound libraries. The ability of the BioMAP® approach to identify countermeasures for general anti-inflammatory agents has been demonstrated. A variety of compound sources have been evaluated including natural product libraries, chemically diverse compound libraries, kinase-focused libraries, nuclear hormone receptor ligand libraries, novel protein libraries, etc. From a test set of ~400 drug-like compounds, ~6% compounds generated BioMAP® profiles that could be associated with a therapeutic hypothesis. FIG. 2 shows the BioMAP® profile of an active compound overlaid with profiles from inactive compounds, demonstrating how active agents can be easily identified as they typically modulate more than one BioMAP® parameters. Active compounds have been identified from a variety of compound collections with an rate of actives ranging from <1% (combichem libraries) to 30% (natural product and kinase focused libraries). Of four novel compounds selected for animal studies (murine delayed-type hypersensitivity), three were subsequently confirmed.

Example 2

Diagnostic Database of Biologic Response Profiles to Known CW or Toxic Agents

The database of profiles provides an essential dataset for functional classification of chemical agent activities, and for development of informatics approaches to characterizing human response pathways and mechanisms, and for screen- BioMAP® Systems useful in profiling CW or toxic agents include those listed in Table 1. These systems cover (1) inflammatory responses (monocyte and macrophage responses, T cell responses, keratinocyte and lung epithelial cell responses, fibroblast responses, fibroblast/epithelial cell interactions, endothelial and smooth muscle cell responses, T-cell/endothelial cell interactions, monocyte/endothelial cell interactions), (2) cell proliferation, (3) tissue remodeling (expression of proteins involved in matrix production and degradation: collagens I and III, TIMPs (tissue inhibitor of metalloproteinase), uPAR (urokinase plasminogen activator receptor), PAI-1 (plasminogen activator inhibitor-1), and (4) thrombosis (expression of proteins involved in thrombosis: tissue factor, thrombomodulin).

The BioMAP® 3C (3 cytokine) system contains human umbilical vein endothelial cells (HUVEC) with IL-1β, TNF-α, and IFN-γ cultured for 24 h in the presence or absence of selected compounds. Readouts are selected for their robust response to one or more of these cytokines or to specific drugs as well as their relevance to vascular inflammation. The BioMAP® 4H System contains HUVEC cultured with IL-4 and histamine for 24 hours. The BioMAP® SAg (superantigen) and LPS (lipopolysaccharide) Systems are multicellular systems comprising peripheral blood mononuclear cells (PBMC; a mixture of CD4+ and CD8+T-cells, monocytes, NK cells, and other mononuclear leukocytes) and endothelial cells, either stimulating the T-cell receptor complex with superantigen (the SAg system), or stimulating toll receptor 4 the LPS system. The HDF3CT and HDFT Systems are fibroblasts cultures stimulated with a combination of IL-1β, TNF-α, IFN-γ and/or TGFβ. The BioMAP® Mphg System is a coculture of macrophages and endothelial cells stimulated with TLR2/6 ligand zymosan. The SMC3C and HUSMC3C Systems are smooth muscle cell and SMC/EC co-cultures stimulated with a combination of IL-1β, and IFN-γ. Parameters tested for Systems are shown in Table 1.

In cell cultures, HUVEC are pooled from multiple donors, cultured according to standard methods, and plated into microtiter plates at passage 4. Human neonatal foreskin fibroblasts (HDFn) from 3 donors are pooled and cultured according to standard methods. 24 h before stimulation with cytokines, confluent HDFn in microtitre plates are serum starved.

Peripheral blood mononuclear cells (PBMC) are prepared from buffy coats from normal human donors according to standard methods. Monocyte-derived macrophages are differentiated in the presence of M-CSF according to standard procedures. Keratinocytes, bronchial lung epithelial cells. Concentrations/amounts of agents added to confluent microtiter plates to build each system: cytokines (IL-1β, 1 ng/ml; TNF-α, 5 ng/ml; IFN-γ, 20 ng/ml; TGFβ, 5 ng/ml; IL-4, 5 ng/ml), activators (histamine, 10 μM; SAg, 20 ng/ml or LPS, 0.2 ng/ml), PBMC ($7.5 \times 10^4$ cells/well) or macrophages ($5 \times 10^4$ cells/well).

Chemical Warfare Agents.

For testing in BioMAP® assays, CW agents from high priority classes are analyzed. Agents include commercially available metabolic/cellular poisons (such as potassium cyanide, and rotenone), acetylcholine esterase inhibitors (the nerve agent diisopropylfluorophosphonate), and a sulfur mustard analog, 2-chloroethylethyl sulfide (CEES). Comparison and reference agents include inhibitors of metabolic function (e.g. DNP, atractyloside, bonkrekic acid, FCCP, malonate, etc.), inducers of apoptosis and necrosis (embellin, doxorubicin, staurosporine, etc.) Agents are tested at concentrations providing a full dose-response curve in BioMAP® systems, as shown in Table 1. These systems cover the biology of vascular inflammation, T cell, monocyte and macrophage activation, as well as aspects of asthma/allergy, lung biology and skin biology. Agents are prepared in suitable buffers, and added 1 hr before stimulation of the cells.

Readout Parameter Measurements.

The levels of most readout parameters are measured by ELISA. Overt cytotoxic effect of agents on cells is determined by 1) measuring alterations in total protein (SRB assay), 2) measuring the viability of peripheral blood mononuclear cells (incorporation of propidium iodide, PI); and 3) microscopic visualization. SRB is performed by staining cells with 0.1% sulforhodamine B after fixation with 10% TCA, and reading wells at 560 nm. PBMC viability is assessed by adding propidium iodide (10 μg/ml) to PBMC that had been cultured for 24 hours in the presence of activators and measuring the percentage of cells that incorporated dye by flow cytometry after 10 minutes. Cells are also assessed visually according to the following scheme: 2.0=cobblestone (unactivated phenotype); 1.0=activated (normal phenotype); 0.5=lacy or sparse; 0.375=rounded; 0.25=sparse and granular; 0.1=no cells in well.

Data Analysis.

Mean optical density values for each parameter are calculated from triplicate samples per experiment. The mean value obtained for each parameter in a treated sample is then divided by the mean value from an appropriate control to generate a ratio. All ratios are then log 10 transformed. 99% prediction envelopes (grey shading in Figures) are calculated for historical controls. This allows the significance levels of any differences to be assessed. Compounds are tested in at least 3 replicate experiments with n=3 for each experiment (n=9 total) to generate mean profiles.

Example 3

Additional Biomap® Systems for Assessment of CW or Toxic Agent-Induced Biologic Responses BioMAP® CW or toxicity testing provides systems targeting chemical threat agent or toxic agent profiling. Many chemical threat agents induce pathology at the epithelial surfaces, as do vesicating agents such as sulfur mustard. BioMAP® systems can be used to model skin and lung tissues by evaluating agent activities in early passage primary human keratinocyte and bronchial epithelial cultures (and co-cultures) under a matrix of environmental conditions, as set forth in Table 1. These systems include keratinocytes, lung epithelial cells, fibroblasts and smooth muscle cell combinations. In addition to inflammatory conditions, other conditions to be evaluated include cellular stress and growth factor conditions because these are known to modulate responses to chemical threat agents. The use of early passage primary cells is important as signaling pathways in cell lines are frequently abnormal. Normal human epithelial keratinocytes (NHEK) differ from a keratinocyte cell line in the response to sulfur mustard. Sulfur mustard induced TNF-α expression in NHEK cells but not in the cell line.

Additional systems may be implemented to evaluate the responses of resting tissues. Systems described in Table 1 are designed to discriminate the mechanisms of drugs, which generally act as inhibitors of biologic pathways. Chemical threat agents can act as inhibitors, or as potent activators of targeted biologic pathways. Responses of resting cell systems provide additional power in detecting and discriminating the MoA of the induced biological responses.

The process includes 1) an initial set of 5-10 input factors (e.g. growth factors, cytokines, other environmental inputs) and 20-40 readout parameters selected from literature sources. The selection criteria include expression data, correlation to disease settings, and known pathway associations. 2) The levels of readout parameters are assessed across a matrix of input factor conditions. Those factor combinations for which multiple readout parameters show robust modulation by individual and multiple factors are selected as initial systems. Those readout parameters that are robustly modulated are identified and selected. 3) a set of pharmacologic or bioactive agents (including chemical threat agents) is tested and the resulting activity profiles assessed for reproducibility and biological coverage (as defined by how many different pathways are active and can be detected and distinguished, for example, as assessed with pathway inhibitors.

Statistical and information theory-based methods are applied to select optimal parameters and combination of parameters for best discrimination of agents (toxic agents, drugs) in the test library. Optimization of systems may continue by the evaluation of new readout parameters, and by assessment of altered conditions (environmental factors that optimize responses will be selected). For each cell type, cells from a number of donors will be tested for their variability in responses. For cell types and parameters where there is significant donor variability, donors can be pooled to produce an average BioMAP®.

Example 4

Computational Methods for MoA/MoT Classification

Overall similarity of profiles is assessed by employing pair wise correlation analysis and multi-dimensional scaling. Different statistical metrics (e.g. Pearson, Euclidian distance, Spearman rank) are applied to identify optimal methods for classification of CW or toxic agent profiles based on clustering of repeat profiles from individual chemical threat agents, and discrimination of BioMAP® CW or toxic profiles from mechanistically distinct agents. These methods allow efficient identification of known agents encountered in the future. More importantly, they determine when a novel agent is substantially similar to known threat agents in the database, allowing immediate selection of appropriate countermeasures.

Example 5

Toxicity Related Pathway Mechanisms in Complex Human Cell Assay Systems

Figure 3:
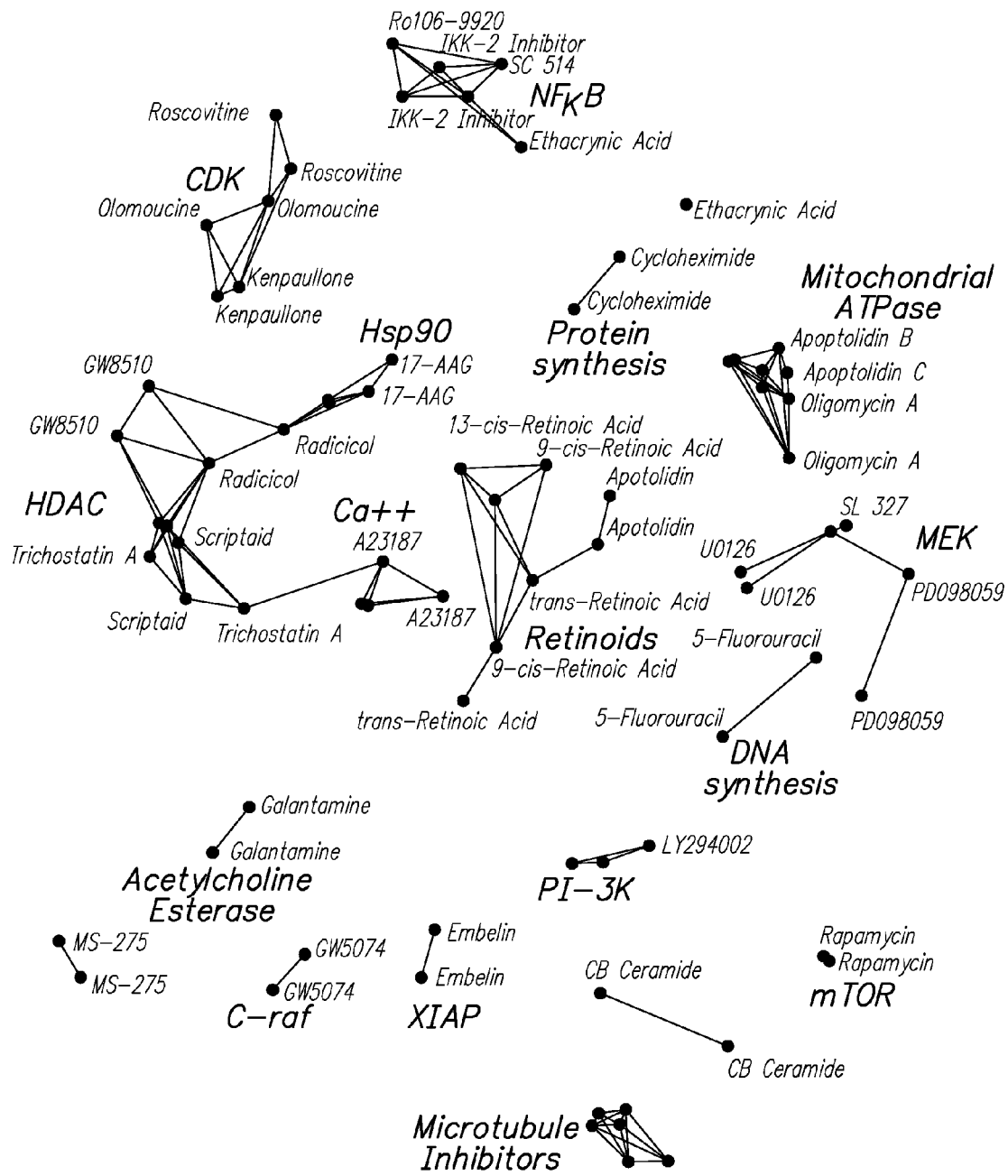

Compounds with various mechanisms of toxicity have been profiled in BioMAP® assay systems. These compounds include inhibitors of mitochondrial function, Shaoguamycin (Piericin A), an inhibitor of NADH-quinone oxidoreductase (Complex I) and oligomycin, an inhibitor of F(0)F(1) ATPase, embelin, an inhibitor of the anti-apoptotic protein XIAP, as well as various relevant signaling pathway inhibitors. These compounds all induce active BioMAP® profiles that cluster according to target mechanism of action upon correlation analysis (FIG. 3, and Table 4). For example, the BioMAP® profiles for the calcium ionophore, A23187, cluster with the BioMAP® profiles generated for thapsigargan, an inhibitor of the endoplasmic reticulum calcium ATPase, both calcium-mobilizing compounds. Also, the profiles for inhibitors of IKK-2 (I kappa kinase-2), a component of the NFκB pathway, cluster with an inhibitor of ubiquitin ligase (Ro106-9920) and ethacrynic acid. Ubiquitin ligase plays a role in NFκB signaling by mediating the degradation of IκB, a cytoplasmic inhibitor of the NFκB components p65 and c-rel. Ethacrynic acid is a reactive electrophile that can modify cellular targets, including NFκB (Kileen, et al., (2005) J. Pharmacol Exp Ther. 316:1070-1079). Many of these mechanisms can cause apoptosis or programmed cell death. Embellin, a specific inhibitor of XIAP, an anti-apoptotic bcl-2 family member induces apoptosis. Ceramide induces non-caspase-dependent programmed cell death (Patschan, (2008) Am J Physiol Heart Circ Physiol. In the press). Oligomycin A and Shaoguamycin B are inhibitors of the mitochondrial electron transport chain, inhibiting ATPase and Complex I, respectively. Compounds targeting other distinct mitochondrial targets, such as cytochrome bc1 are also active and distinguishable in BioMAP® systems. FIG. 4 shows the BioMAP® profile of the Complex III inhibitor, myxathiazol.

BioMAP® systems are of interest with respect to assessing compound activities resulting from chemical reactivity or metabolic activation. In a number of BioMAP® systems, cells are stimulated with combinations of activators that induce a highly oxidative environment that may promote these reactions. FIG. 5 shows the BioMAP® profile of wortmannin, an inhibitor of P1-3 kinase that also has the potential for chemical reactivity (Yuan, 2007). The BioMAP® profile of wortmannin in endothelial cell-containing systems (3C, LPS, and Sag) is not cytotoxic and profile activities reflect inhibition of PI-3 kinase (Kunkel, 2004a,b). In contrast, in fibroblast-containing systems, wortmannin shows selective cytotoxicity to fibroblasts under inflammatory conditions (HDF3CGF and HDF3C), but not non-inflammatory settings (/HDFNo and /HDFT). This cytotoxicity is not shared by other PI-3 kinase inhibitors and likely reflects compound specific effects.

Among cellular targets of chemically reactive compounds, Keap2 and NFkappaB are frequent targets of electrophilic attack, containing free thiols that are sensitive to covalent modification. Keap2 is an intracellular cytoskeletal protein that functions as an electrophile sensor, and under normal conditions, binds and inhibits the transcription factor Nrf2. Upon covalent modification, Keap1 releases Nrf2 which then enters the nucleus, binds to anti-oxidant response elements (ARE) and induces the transcription of metabolic phase 2 enzymes including glutamate-cysteine ligase, the rate-limiting enzyme in glutathione synthesis, heme oxygenase-1, NADPH:quinone oxidoreductase (NQO1), and others. Drugs and bioactive agents that are chemically reactive with NFκB or Keap2 generate specific BioMAP® profiles and are often cytotoxic in inflammatory BioMAP® systems. FIG. 6 shows the BioMAP® profile for ethacrynic acid, an electrophile that induces Nrf2 and also inhibits NFκB (Kileen, 2005). While ethacrynic acid has been used clinically as a loop diuretic that inhibits the Na+−K+−2Cl— cotransporter, it also produces serious gastrointestinal side effects.

TABLE 4

Compounds of various toxicity mechanisms profiled in BioMAP ® Systems.

| Compound | Conc (µM) | Target/Mechanism |
|---|---|---|
| Galantamine | 30, 90 | Acetylcholine Esterase |
| A23187 | 0.3, 1 | $Ca^{++}$ ionophore |
| Roscovitine | 2.7, 8.3 | CDK |
| Olomoucine | 11, 33 | CDK |
| Kenpaullone | 3, 10 | CDK |
| GW8510 | 8.3, 25 | CDK |
| GW5074 | 8.3, 10 | C-Raf |
| 5-Fluorouracil | 30, 90 | DNA Synthesis |
| Thapsigargan | 0.1, 0.3 | ER $Ca^{++}$ ATPase |
| Apoptolidin | 0.03, 0.1 | Mito. F(0)F(1) ATPase |
| Apoptolidin B | 1, 3 | Mito. F(0)F(1) ATPase |
| Apoptolidin C | 1, 3 | Mito. F(0)F(1) ATPase |
| Oligomycin A | 1, 3 | Mito. F(0)F(1) ATPase |
| Shaoguamycin B | 0.3, 1 | Mito. Complex I |
| Ethacrynic Acid | 3.3, 10 | Glutathione S-transferase |
| M344 | 10, 30 | Histone deacetylase |
| Scriptaid | 3.3, 10 | Histone deacetylase |
| Trichostatin A | 0.3, 1.1 | Histone deacetylase |
| MS-275 | 10, 30 | Histone deacetylase |
| Geldanamycin | 1.1, 3.3 | Hsp90 |
| 17-AAG | 1.1, 3.3 | Hsp90 |
| Radicicol | 3.3, 10 | Hsp90 |
| IKK-2 Inhibitor IV | 0.37, 1.1 | IKK-2 |
| SC-514 | 16, 50 | IKK-2 |
| SL 327 | 3.3, 10 | Mek |
| UO126 | 3.3, 10 | Mek |
| PD098059 | 10, 30 | Mek |
| Rapamycin | 0.3, 1 | mTOR |
| Wortmannin | 3.3, 10 | PI-3 kinase |
| Ly294002 | 3.3, 10 | PI-3 kinase |
| C8 Ceramide | 3.3, 10 | PKC Activator |
| Ro106-9920 | 1.8 | Proteasome Inhibitor |
| Cycloheximide | 0.3, 1.1 | Protein Synthesis |
| Trans-retinoic acid | 7.4, 22 | RAR/RXR |
| 9-cis-Retinoic Acid | 30, 33 | RAR/RXR |
| 13-cis-Retinoic Acid | 11, 33 | RAR/RXR |
| Epitholone B | 0.3, 1 | Tubulin |
| Epitholone D | 0.3, 1 | Tubulin |
| Paclitaxel | 0.3, 1.1 | Tubulin |
| Embelin | 30, 90 | XIAP |

What is claimed is:

1. A method of classification of toxic agents and effective countermeasures according to their mechanism of toxicity, the method comprising:
    recording changes in at least three different cellular parameter readouts as a result of introduction of the toxic agent in a toxicity system comprising primary human cells cultured in the presence of at least one factor activating a signaling pathway and wherein said profile comprises control data from said toxicity system lacking said agent;
    deriving a biological dataset profile from the changes in parameter readouts, where the biological dataset profile comprises data normalized to be a ratio of test to control data in the toxicity system under control conditions in the absence of the toxic agent, and the output from 3 or more parameters are sufficient to discriminate the mechanism of toxicity of said toxic agent; and analyzing the biological dataset profile by a multiparameter pattern recognition algorithm to quantify relatedness of the biological dataset profile to reference biological dataset profiles that include known toxic agents that target specific pathways, wherein the presence or absence of relatedness to said reference biological dataset profiles provides a classification of said agent's mechanism of toxicity; and using the classification of the agent according to its mechanism of toxicity to select an effective countermeasure agent that protects cellular pathways targeted by the toxic agent.

2. The method according to claim 1, wherein said toxic agent is a chemical or biological warfare agent, metabolic poison, vesicant or nerve agent.

3. The method according to claim 1, wherein the toxic agent is an environmental toxin.

4. The method according to claim 1, wherein said biological dataset profile comprises readouts from a toxicity system selected from:

(a) primary human endothelial cells cultured in the presence of two or more factors selected from TNF-a; IL-1; IFNg; thrombin; oxidized lipids; angiotensin-II; endothelin-1; aldosterone; IL-4; IL-13; TGFb; histamine; glucose, and insulin; and readouts from 3 or more parameters selected from E-selectin, VCAM-1, ICAM-1, MCP-1, MIG, IL-8, HLA-DR, uPAR, CD141/thrombomodulin, and CD142/Tissue Factor;

(b) primary human endothelial cells in a coculture with peripheral blood mononuclear cells, with a factor stimulating the toll receptor 4 (TLR4); and readouts from 3 or more parameters selected from CD14, CD142, CD40, CD69, MCP-1, E-selectin, IL-1a, IL-8, M-CSF, VCAM-1, CD25, thrombomodulin, and tissue factor;

(c) primary human endothelial cells in a coculture with peripheral blood mononuclear cells, with a superantigen; and readouts from 3 or more parameters selected from CD38, CD40, CD69, CD154/CD40L, E-selectin, IL-8, MCP-1, and MIG;

(d) primary human fibroblasts, early passage primary human keratinocytes or a combination of the two cultured with a combination of IL-1β, TNF-α, IFN-γ and/or TGFβ; and readouts from 3 or more parameters selected from MCP-1 (monocyte chemoattractant protein-1), ICAM-1 (intracellular cell adhesion molecule-1), collagen I, collagen III, IP-10, Mig, M-CSF (macrophage colony stimulating factor), MMP-9, PAI-1, TGFb1, TIMP-1, uPA, uPAR, I-TAC, HLA-DR, IL-1a, keratin 8/18, MMP-1, eotaxin-3, and IL-8;

(e) macrophages and endothelial cells co-cultured with TLR2/6 ligand zymosan; and readouts from 3 or more parameters selected from MCP-1, ICAM-1, collagen I, collagen III, IP-10, Mig, M-CSF, MMP-9, PAI-1, TGFb1, TIMP-1, uPA, uPAR, I-TAC, HLA-DR, IL-1a, keratin 8/18, MMP-1, Eotaxin-3, and IL-8;

(f) primary human bronchial epithelial cells stimulated with IL-1, TNF and IFNg; or TNF, IL4 and IL-13; and readouts from 3 or more parameters selected from MCP-1, ICAM-1, collagen I, collagen III, IP-10, Mig, M-CSF, MMP-9, PAI-1, TGFb1, TIMP-1, uPA, uPAR, I-TAC, HLA-DR, IL-1a, keratin 8/18, MMP-1, Eotaxin-3, and IL-8; and (g) smooth muscle cells, optionally co-cultured with endothelial cells, stimulated with IL-1β, TNF, and IFN-γ; and readouts from 3 or more parameters selected from MCP-1, ICAM-1, collagen I, collagen III, IP-10, Mig, M-CSF, MMP-9, PAI-1, TGFb1, TIMP-1, uPA, uPAR, I-TAC, HLA-DR, IL-1a, keratin 8/18, MMP-1, Eotaxin-3, and IL-8.

5. The method according to claim 1, wherein the biological dataset profile for the toxic agent, comprises output from a plurality of toxicity systems.

6. The method according to claim 5, wherein the plurality of toxicity systems are concatenated for simultaneous analysis.

7. The method according to claim 5, wherein said toxicity system comprises one or more of cells from an inflammatory context selected from toxicity systems (a), (b), (c) (d) and (e).

8. The method of claim 5, wherein said toxicity system comprises one or more cells from an epithelial surface context of toxicity system (f).

* * * * *

UNITED STATES PATENT AND TRADEMARK OFFICE
CERTIFICATE OF CORRECTION

| | |
|---|---|
| PATENT NO. | : 8,718,945 B2 |
| APPLICATION NO. | : 12/594192 |
| DATED | : May 6, 2014 |
| INVENTOR(S) | : Ellen L. Berg |

It is certified that error appears in the above-identified patent and that said Letters Patent is hereby corrected as shown below:

IN THE CLAIMS:

Column 30, line 31 (Claim 5, line 1), "according to claim 1" should read --according to claim 4--.

Signed and Sealed this
Twenty-third Day of September, 2014

Michelle K. Lee
*Deputy Director of the United States Patent and Trademark Office*